(12) United States Patent
Wilcox

(10) Patent No.: US 11,540,753 B1
(45) Date of Patent: Jan. 3, 2023

(54) BLOOD HEALTH MONITORING METHOD AND DEVICE

(71) Applicant: Clinton Bud Wilcox, Grass Valley, CA (US)

(72) Inventor: Clinton Bud Wilcox, Grass Valley, CA (US)

(73) Assignee: Scosche Industries, Inc., Oxnard, CA (US)

( * ) Notice: Subject to any disclaimer, the term of this patent is extended or adjusted under 35 U.S.C. 154(b) by 0 days.

(21) Appl. No.: 17/891,024

(22) Filed: Aug. 18, 2022

Related U.S. Application Data

(60) Provisional application No. 63/235,642, filed on Aug. 20, 2021.

(51) Int. Cl.
| | |
|---|---|
| *A61B 5/08* | (2006.01) |
| *A61B 5/145* | (2006.01) |
| *A61B 5/00* | (2006.01) |
| *A61B 5/097* | (2006.01) |
| *A61B 10/00* | (2006.01) |

(52) U.S. Cl.
CPC .......... *A61B 5/14532* (2013.01); *A61B 5/082* (2013.01); *A61B 5/097* (2013.01); *A61B 5/742* (2013.01); *A61B 5/746* (2013.01); *A61B 2010/0087* (2013.01); *A61B 2560/0214* (2013.01)

(58) Field of Classification Search
CPC ..... A61B 5/14532; A61B 5/082; A61B 5/097; A61B 5/742; A61B 5/746; A61B 2010/0087; A61B 2560/0214
See application file for complete search history.

(56) References Cited

U.S. PATENT DOCUMENTS

| | | | |
|---|---|---|---|
| 2021/0338142 A1* | 11/2021 | Arnold | G01N 30/60 |
| 2022/0007972 A1* | 1/2022 | Thors | A61B 5/097 |

* cited by examiner

*Primary Examiner* — Andrey Shostak
(74) *Attorney, Agent, or Firm* — Temmerman Law; Mathew J. Temmerman

(57) ABSTRACT

A wearable analyte breath alert device and method for non-invasive monitoring of an analyte in a sample from a user. The device comprises an outer casing, a forward face having an in-line insignia, a front port and an activation button, a rear face having a detector threshold region, a side port and a LED indicator, a reversible core having a main processor module and a volatile organic compound (VOC) sensor adaptable to detect at least one volatile organic compound of the user. The VOC sensor further comprises a central sensor circuit having at least one nano gas sensor, a sensor signal conditioning unit and an A/D interface. The central sensor circuit is operably connected to a Bluetooth Low Energy (BLE) element having a microcontroller. An alarm component is coupled with the BLE element that alerts the user based on the analyte detected by the nano gas sensor.

7 Claims, 20 Drawing Sheets

BLOOD HEALTH MONITORING METHOD AND DEVICE

RELATED APPLICATIONS AND PRIORITY

This application claims priority from U.S. provisional patent application 63/235,642, filed Aug. 20, 2021, which is incorporated by reference herein as if set out in full.

BACKGROUND OF THE DISCLOSURE

Technical Field of the Disclosure

The present invention relates generally to a device and methods for blood aerosolized analyte measurement, and more particularly to a device and a method for monitoring the presence, amount, and/or concentration of a chemical species in a gaseous sample wherein the chemical species is selected to be indicative of/or related to a physiological status of a user, for example the blood glucose level or volatile organic compound level in a user's breath.

Description of the Related Art

Traditional personal health monitors may be bulky, rigid, and uncomfortable—generally not suitable for use during daily physical activity or continuous use throughout the working day. As such, improved means for collecting, storing and analyzing personal health and environmental information are needed. In addition, improved ways of distributing raw and analyzed personal health information are desirable to support efforts to enhance healthcare quality and reduce costs. Traditional personal health monitors are adapted to facilitate measurement and management of a variety of conditions, including diabetes.

Diabetes is a disease in which an amount of glucose in the blood of a patient is excessively small or excessively large. Diabetes may develop when insulin production is dysregulated in the bloodstream, pancreas and related organs. In addition, diabetes may develop when secreted insulin action is dysregulated often due to dietary and/or genetic factors. For example, consider a subject with type 1 diabetes.

In order to adequately manage type 1 diabetes, the subject is required to monitor blood glucose concentrations accurately and at regular intervals through the day. If blood glucose concentrations are too high (hyperglycemia) or too low (hypoglycemia), corrective action on the part of the subject must be taken to avoid serious consequences. As is well known in the art, hypoglycemia can result in seizures, coma, and even death.

Traditionally, blood glucose levels are measured by collecting a blood sample and subsequently directly measuring a concentration of glucose in the collected blood sample. However, a user often feels pain when his or her skin is stuck by a needle, for example, during the collection of a blood sample.

Further to the above, many individuals suffer from non-diabetic conditions that require routine monitoring of an aerosolized analyte (i.e., determining the concentration of the gas phase analyte). For example, continuous measurement of volatile organic compounds ("VOCs") can indicate that a subject is suffering from or likely to suffer from a given disease or condition such as impending heart attack. In addition, various studies report a correlation between one or more analytes and a given disease or condition rather than a causative link between an analyte and a condition. This fact suggests that continuous measurement of aerosolized compounds has a wide array of applications. By monitoring one or more analytes related to, for example, VOCs associated with hypothyroidism, a subject may be alerted that he/she is in danger of hypothyroid related arrhythmias, weight gain, or decreases in blood pressure.

Furthermore, an increasingly large percentage of total healthcare spending is allocated to the care and treatment of subjects with conditions that may be ameliorated by continuous monitoring. In particular, healthcare costs are rising for those individuals that do not adequately monitor their atherosclerosis-related conditions (i.e., an angina patient who fails to adequately monitor C-Reactive Protein).

One reason patients fail to monitor such conditions is that monitoring can be painful (i.e., a finger stick), physically cumbersome, expensive, and requires the user to seek out poorly marketed special equipment that often must be transported to the user. In addition, in many cases requiring monitoring, the prescribed frequency of monitoring intervals is so high that patients choose to forgo monitoring entirely.

Thus, the devices and methods of the prior art suffer from drawbacks and shortcomings that result in decreased monitoring in patient populations that benefit significantly from continuous monitoring.

Therefore, there is a need for a device and a method for measuring blood glucose continuously and without the need to collect a liquid blood sample. Such a needed device and method would non-invasively monitor a user's blood glucose level by measuring aerosolized acetone and similar volatile organic compounds indicative of glucose levels from the breath of the user. Further, such a device and method would alert the user based on set high and low glucose levels. Moreover, such a device and method would provide a variety of means to alert the user including haptic, LED light array, programmable voice alert, and alert to a smart device. Such a device and method would have an automated means of communicating dangerous glucose levels to third parties through. Moreover, such a device and method would monitor blood glucose concentrations accurately and at regular intervals through the day to avoid serious health consequences. Further, such a device and method would provide a painless, small, cost effective, stylish and highly functional device that can be worn by the user. The present embodiment overcomes shortcomings in the field by accomplishing these critical objectives.

SUMMARY OF THE DISCLOSURE

To minimize the limitations found in the prior art, and to minimize other limitations that will be apparent upon the reading of the specification, the present application provides a method and a device to alert a user based on the concentration of an analyte in a sample from the breath of the user. The present application provides a wearable analyte breath alert device for non-invasive monitoring of the concentration of glucose in an aerosolized volatile organic compound from the breath of the user. The sample can be any aerosolized gas or fluid that emanates from the user and contains the analyte. The analyte can be selected from a group consisting of: glucose, acetone, ketone or any volatile organic compound.

The device comprises an outer casing, a forward face, a rear face opposite thereto, a reversible core, a volatile organic compound (VOC) sensor and a securement means. The outer casing is made of materials selected from a group consisting of: Polycarbonate/acrylonitrile butadiene styrene (PC/ABS) plastics, silicone rubber, and nylon. The forward face is secured to the outer casing and includes an in-line insignia, a front port and an activation button. The rear face is opposite the forward face and is secured to the outer casing. The rear face includes a detector threshold region, a side port and a LED indicator. The front port and the detector threshold region is configured to function as gas sensor intake ports, speaker ports, Bluetooth sensors and/or cooling ports or evacuation/purge ports for purging or evacuating a previous breath sample from the device. The reversible core includes a main processor and is positioned in between the outer casing, the forward face and the rear face. The volatile organic compound (VOC) sensor is adaptable to detect at least one volatile organic compound of the user. The VOC sensor is positioned on the main processor module. The VOC sensor includes a central sensor circuit operably connected to a Bluetooth Low Energy (BLE) element having a microcontroller, an alarm component and a DC to DC element having a battery charger and a battery. The central sensor circuit further comprises a gas sensor unit having at least one nano gas sensor and at least one heater, a sensor signal conditioning unit having a gain element and a conversion element, and an A/D interface having an analog to digital converter and a digital to analog converter. The at least one nano gas sensor is extremely sensitive and detects the analyte present in the sample. The alarm component includes an audio piezo actuator, a vibration element, and a tri-color light emitting diode (LED). The alarm component further includes an alarm timing means that allows the user to program alerts and record glucose levels at regular intervals. The alarm component alerts the user based on the detected analyte at intervals controlled by the user or on demand. The outer casing is adaptable to attach with the securement means and the securement means is configured to attach the device with the user. In the preferred embodiment, the securement means is a neck securement means and the preferred device is a necklace. The securement means includes a fitting means including a snap fitting and/or magnetic engagement fitting means. Notably, the fitting means may further include a screw fit and/or adhesive engagement means. In an alternate embodiment, the securement means can be a wrist securement, and/or a clothing clipping securement. In an alternate embodiment, the device can be a wristwatch and/or a device adaptable to attach to a clothing. In the alternate embodiment, the wristwatch, includes a wrist securement, a watch casing and a plurality of clasping holes, and neck securement.

The present application provides a method for detecting acetone, ketones and other volatile organic compounds present in the breath of the user and alerts the user based on the concentration of acetone, ketones and other volatile organic compounds. The method comprises the steps of: providing a wearable analyte breath alert device having a front port, a detector threshold region, a volatile organic compound (VOC) sensor operably coupled to a Bluetooth Low Energy (BLE) element having a microcontroller and an alarm component for non-invasive monitoring of an analyte in a sample from a user. Then, introducing the sample to the VOC sensor through the front port and the detector threshold region of the wearable analyte breath alert device. Introducing the sample to the VOC sensor includes introducing the user's breath onto the front port and the detector threshold region of the wearable analyte breath alert device. The method detects the presence of the analyte in the sample by an at least one nano gas sensor in the VOC sensor and generates a signal by the at least one nano gas sensor based on the presence, amount and concentration of the analyte in the sample. Then transmitting the signal to the microcontroller of the BLE element and the microcontroller analyze the signal to produce a result. Finally, the alarm component alerts the user based on the result from the microcontroller.

A first objective of the present embodiment is to provide a device and a method for measuring blood glucose continuously and without the need to collect a liquid blood sample.

A second objective of the present embodiment is to provide a device and a method that non-invasively monitors a user's blood glucose level by measuring aerosolized acetone and similar volatile organic compounds indicative of glucose levels from the breath of the user.

A third objective of the present embodiment is to provide a device and method that alerts the user based on set high and low glucose levels.

Yet another objective of the present embodiment is to provide a device and method that provides a variety of means to alert the user including haptic, LED light array, programmable voice alert, and alert to a smart device.

Yet another object of the present embodiment is to provide a device and method that provides an automated means for communicating dangerous glucose levels to third parties through the smart device.

Yet another object of the present embodiment is to provide a device and method that monitors blood glucose concentrations accurately and at regular intervals through the day to avoid serious health consequences.

Yet another object of the present embodiment is to provide a device and method that provides a painless, small, cost effective, stylish and highly functional device that can be worn by the user.

These and other advantages and features of the present invention are described with specificity so as to make the present invention understandable to one of ordinary skill in the art.

BRIEF DESCRIPTION OF THE DRAWINGS

In order to enhance their clarity and improve the understanding of the various elements and embodiment shown herein, the figures have not necessarily been drawn to scale. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE DRAWINGS

Figure 1B:
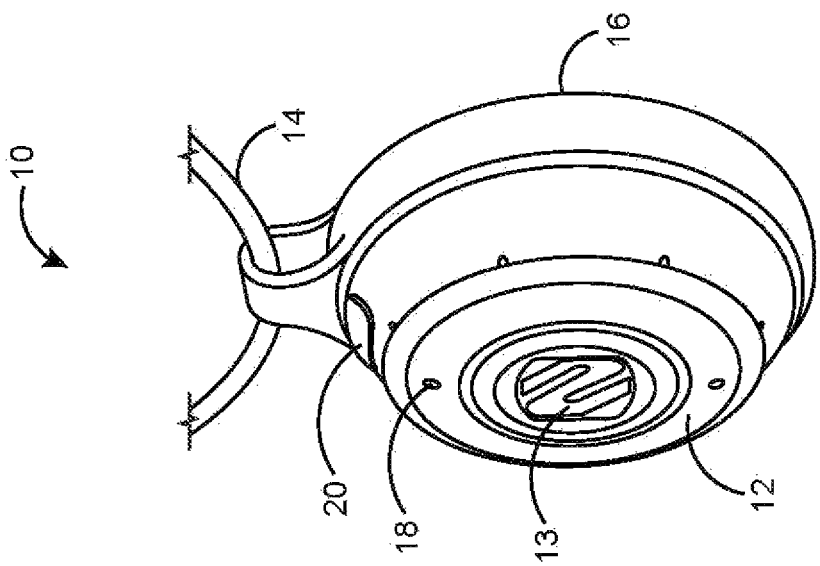
FIG. 1B illustrates a front perspective view of the wearable analyte breath alert device in accordance with the preferred embodiment of the present invention.

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term 'about" means+/−10% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Referring to FIGS. 1A-10, a wearable analyte breath alert device 10 for non-invasive monitoring of an analyte in a sample from a user is illustrated. The preferred embodiment provides a breath alert device 10 which is more specifically a wearable non-invasive glucose breath alert device 10 used to alert the user of high or low blood sugar. The wearable analyte breath alert device 10 is configured to measure aerosolized volatile organic compounds or similar compounds.

The sample can be any aerosolized gas or fluid that emanates from the user and contains the analyte (i.e., gaseous or fluid aerosolized blood). In one embodiment, the sample is an indirect sample. An indirect sample is a sample that is not introduced directly into the inlet ports of the breath alert device 10 by the user (for example, the user breathing through a tube into the inlet ports of the breath alert device 10). In one embodiment, the sample is co-mingled with the ambient environment of the user (for example, ambient air) before being introduced into the breath alert device 10. In a particular embodiment, the sample is ambient air that surrounds the breath alert device 10 and the user. When the sample is ambient air, the analyte originates from or is derived from the user of the breath alert device 10 and becomes mixed with ambient air such that the target analyte is contained in the ambient air surrounding the user. For example, the user of the breath alert device 10 may exhale the analyte in breath, excrete the analyte through skin (VOCs are volatile at body temperature), excrete the analyte through perspiration, excrete the analyte through eccrine glands, apocrine glands, and/or sebaceous glands, or any combination of the foregoing, such that the analyte is mixed with the ambient air.

As described above, the sample may also be a direct sample meaning that the user directly introduces the sample into the breath alert device 10 (i.e., breathes into the inlets ports). A direct sample may be useful for calibrating the breath alert device 10 or may be required when the user is in an environment where an indirect sample is not feasible (for example, when the user is in a high wind environment or a closed environment with a high concentration of VOCs or other compounds that interfere with the detection of the analyte). In certain embodiments, the sample is ambient air containing an analyte emanating from the user (for example, an analyte contained in an exhaled breath or excreted from the user). In certain embodiments, the sample is exhaled breath. In certain embodiments the sample is exhaled breath and the sample is directly introduced into the breath alert device 10 by the user (for example, the user exhales a breath directly into the inlet ports of the device 10).

The analyte can be selected from a group consisting of: glucose, acetone, ketone or any volatile organic compound. In a preferred embodiment, the analyte detected by the breath alert device 10 is glucose, acetone, a VOC, or the like. Notably, the composition of emitted compounds, particularly VOCs, can differ between healthy individuals and individuals with a specific disease or condition and can be indicative or related to a given physiological status of the user.

In one embodiment, the analyte is present in the sample at a concentration greater than or equal to 1 part per billion (ppb) and less than or equal to 1000 parts per million (ppm). In another embodiment, the analyte is present in the sample at a concentration greater than or equal to 1 part per ppb and less than or equal to 100 ppm. In another embodiment, the analyte is present in the sample at a concentration greater than or equal to 1 part per ppb and less than or equal to 10 ppm. In another embodiment, the analyte is present in the sample at a concentration greater than or equal to 10 parts per ppb and less than or equal to 1000 ppm. In another embodiment, the analyte is present in the sample at a concentration greater than or equal to 100 parts per ppb and less than or equal to 1000 ppm. In another embodiment, the analyte is present in the sample at a concentration greater than or equal to 1 part per ppm and less than or equal to 1000 ppm. In another embodiment, the analyte is present in the sample and detected by the breath alert device 10 at a concentration between 1 part per ppb and 10 ppm. In another embodiment, the analyte is present in the sample at a concentration between 1 part per ppb and 750 ppb.

Many VOCs emitted by humans have been correlated with certain diseases. Therefore, in certain embodiments, the analyte is a VOC. A variety of VOCs may be detected by the breath alert device 10 of the present application. In one embodiment, any VOC known in the art to be associated with a physiological status, a predisposition of a physiological status, a disease or condition, or a predisposition to a disease or condition may be detected. In one embodiment, a VOC is any carbon based compound with a vapor pressure greater than 0.01 kPa at 293.15 K (20° C.).

In one embodiment, the analyte is a VOC and the VOC is present in the sample and detected by the breath alert device 10 at a concentration greater than or equal to 1 part per billion (ppb) and less than or equal to 1000 parts per million (ppm). In another embodiment, the analyte is a VOC and the VOC is present in the sample at a concentration greater than or equal to 1 part per ppb and less than or equal to 100 ppm.

In another embodiment, the analyte is a VOC and the VOC is present in the sample at a concentration greater than or equal to 1 part per ppb and less than or equal to 10 ppm. In another embodiment, the analyte is a VOC and the VOC is present in the sample at a concentration greater than or equal to 10 parts per ppb and less than or equal to 1000 ppm. In another embodiment, the analyte is a VOC and the VOC is present in the sample at a concentration greater than or equal to 100 parts per ppb and less than or equal to 1000 ppm. In another embodiment, the analyte is a VOC and the VOC is present in the sample at a concentration greater than or equal to 1 part per ppm and less than or equal to 1000 ppm. In another embodiment, the analyte is a VOC and the VOC is present in the sample at a concentration between 1 part per ppb and 10 ppm. In another embodiment, the analyte is a VOC and the VOC is present in the sample at a concentration between 1 part per ppb and 750 ppb.

In certain embodiments, a single VOC is detected by the breath alert device 10. In other embodiments, more than a single VOC is detected by breath alert device 10 of the present application. In one embodiment, the VOC detected is acetone, methyl nitrate, pentyl nitrate (for example, 2-pentyl nitrate), ethanol, methanol, propanol, methane, propane, ethyl benzene, isoprene, O-xylene (ortho-xylene), formaldehyde, acetaldehyde, or any combination of the foregoing. In another embodiment, the VOC detected is acetone, methyl nitrate, pentyl nitrate (for example, 2-pentyl nitrate), ethanol, methanol, propanol, methane, propane, ethyl benzene, isoprene or any combination of the foregoing.

In another embodiment, the detected VOC is acetone and methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde, or any combination of the foregoing. In another embodiment, the detected VOC is acetone and methyl nitrate, pentyl nitrate (for example, 2-pentyl nitrate), ethanol, methanol, propanol, methane, propane, ethyl benzene, isoprene, or any combination of the foregoing. In another embodiment, the detected VOC is acetone and pentyl nitrate (for example, 2-pentyl nitrate), methanol, propane, isoprene, or any combination of the foregoing. In another embodiment, the detected VOC is one or more of acetone, pentyl nitrate (for example, 2-pentyl nitrate), methanol, propane, or isoprene. In another embodiment, the detected VOC is each acetone, pentyl nitrate (for example, 2-pentyl nitrate), methanol, propane, or isoprene.

In another embodiment, the detected VOC is ethanol and methyl nitrate, pentyl nitrate (for example, 2-pentyl nitrate), acetone, methanol, propanol, methane, propane, ethyl benzene, isoprene, 0-xylene, M/P-xylene, formaldehyde, acetaldehyde, or any combination of the foregoing. In another embodiment, the detected VOC is ethanol and methyl nitrate, pentyl nitrate (for example, 2-pentyl nitrate), ethanol, acetone, propanol, methane, propane, ethyl benzene, isoprene, or any combination of the foregoing. In another embodiment, the detected VOC is ethanol and one or more of methyl nitrate or ethyl benzene. In another embodiment, the detected VOC is each of ethanol, methyl nitrate and ethyl benzene.

In another embodiment, the detected VOC by the breath alert device 10 is isoprene and acetone, methyl nitrate, pentyl nitrate (for example, 2-pentyl nitrate), ethanol, methanol, propanol, methane, propane, ethyl benzene, formaldehyde, acetaldehyde, or any combination of the foregoing. In certain embodiments, the VOC detected is acetone and optionally 1 or more additional VOCs. In certain embodiments, the VOC detected is isoprene and optionally 1 or more additional VOCs. In certain embodiments, the VOC detected is methyl nitrate and optionally 1 or more additional VOCs. In certain embodiments, the VOC detected is pentyl nitrate (for example, 2-pentyl nitrate) and optionally 1 or more additional VOCs. In certain embodiments, the VOC detected is ethanol and optionally 1 or more additional VOCs. In certain embodiments, the VOC detected is methanol and optionally 1 or more additional VOCs. In certain embodiments, the VOC detected is propanol and optionally 1 or more additional VOCs. In certain embodiments, the VOC detected is methane and optionally 1 or more additional VOCs. In certain embodiments, the VOC detected is propane and optionally 1 or more additional VOCs. In certain embodiments, the VOC detected is ethyl benzene and optionally 1 or more additional VOCs. In certain embodiments, the VOC detected is O-xylene and optionally 1 or more additional VOCs. In certain embodiments, the VOC detected is M/P-xylene and optionally 1 or more additional VOCs. In certain embodiments, the VOC detected is formaldehyde and optionally 1 or more additional VOCs. In certain embodiments, the VOC detected is acetaldehyde and optionally 1 or more additional VOCs.

When more than one VOC is detected by the breath alert device 10 at least 2 VOCs may be detected, at least 3 VOCs may be detected, at least 4 VOC may be detected, at least 5 VOCs may be detected, at least 6 VOCs may be detected, at least 7 VOCs may be detected, at least 8 VOCs may be detected, at least 9 VOCs may be detected, or more than 9 VOCs may be detected. In the foregoing, the upper range for the number of VOCs detected may be 15, 20, 25 or 50 VOCs. Therefore, as one example, when at least 2 VOCs are detected, from 2 to 15 VOCs, from 2 to 10 VOCs, from 2 to 5 VOCs, from 2 to 4 VOCs, or from 2 to 3 VOCs may be detected by the sensor system.

While the present disclosure provides for the detection of VOCs regardless of the reason why such VOC is associated with a particular physiological status, scientific principles may inform what VOCs may be associated with a particular physiological status. Human breath is composed of inhaled air, $CO_2$, water vapor, small amounts of proteins, and VOCs. The VOCs are created through a variety of physiological process and non-physiological processes, including, but not limited to, internal metabolic reactions, metabolic reactions from bacteria or other organisms present in the body, as gases produced for physiological signaling roles, or as metabolites from inhaled atmospheric components. By way of example only, the following provides a scientific basis for the utility of selected VOCs in the determination of a hypoglycemia. Pentyl nitrate (for example, 2-pentyl nitrate) and methyl nitrate may be generated through pathways involving organic peroxy radical, superoxide ion, or other byproducts of oxidative reactions. As oxidative stress is associated with hypoglycemia, levels of these compounds may reflect changes in oxidative status indicative of hypoglycemia.

Ethanol methanol, propanol, and propane production may be due activity of gut flora bacteria (for example, alcoholic fermentation of glucose by gut bacteria and yeast). As such, the levels of ethanol raid methanol are responsive to fluctuations in glucose concentration. Ethyl benzene, O-xylene, and M/P-xylene are generally inhaled, partly metabolized by liver, and then exhaled at lower concentration. Rapid-onset hyperglycemia may suppress hepatic metabolism causing increased concentration of these compounds in exhaled air. In one embodiment, the physiological status detected by the breath alert device 10 is hypoglycemia and the VOC is acetone, methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde or combinations of the foregoing.

In certain embodiments, the physiological status is hypoglycemia and the VOC detected is: (1) acetone, methyl nitrate, pentyl nitrate (for example, 2-pentyl nitrate), ethanol, methanol, propanol, methane, propane, ethyl benzene, isoprene, O-xylene, M/P-xylene formaldehyde, acetaldehyde, or any combination of the foregoing; (2) acetone, methyl nitrate, pentyl nitrate (for example, 2-pentyl nitrate), ethanol, methanol, propanol, methane, propane, ethyl benzene, isoprene or any combination of the foregoing; (3) acetone and methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde, or any combination of the foregoing; (4) acetone and methyl nitrate, pentyl nitrate (for example, 2-pentyl nitrate), ethanol, methanol, propanol, methane, propane, ethyl benzene, isoprene, or any combination of the foregoing; (5) acetone and pentyl nitrate (for example, 2-pentyl nitrate), methanol, propane, isoprene, or any combination of the foregoing; (6) ethanol and methyl nitrate, pentyl nitrate (for example, 2-pentyl nitrate), acetone, methanol, propanol, methane, propane, ethyl benzene, isoprene, O-xylene, M/P-xylene, formaldehyde, acetaldehyde, or any combination of the foregoing; (7) ethanol and methyl nitrate, pentyl nitrate (for example, 2-pentyl nitrate), ethanol, acetone, propanol, methane, propane, ethyl benzene, isoprene, or any combination of the foregoing; (8) ethanol and methyl nitrate, ethyl benzene, or any combination of the foregoing; (9) isoprene and acetone, methyl nitrate, pentyl nitrate (for example, 2-pentyl nitrate), ethanol, methanol, propanol, methane, propane, ethyl benzene, O-xylene, M/P-xylene, formaldehyde, acetaldehyde, or any combination of the foregoing; 10) ethanol, methyl nitrate, and ethyl benzene; or 11) acetone, pentyl nitrate (for example, 2-pentyl nitrate), methanol, propane, and isoprene.

In certain embodiments, the physiological status is hypoglycemia and the VOC detected is acetone and optionally 1 or more additional VOCs. In certain embodiments, the physiological status is hypoglycemia and the VOC detected is isoprene and optionally 1 or more additional VOCs. In certain embodiments, the physiological status is hypoglycemia and the VOC detected is methyl nitrate and optionally 1 or more additional VOCs. In certain embodiments, the physiological status is hypoglycemia and the VOC detected is pentyl nitrate (for example, 2- pentyl nitrate) and optionally 1 or more additional VOCs. In certain embodiments, the physiological status is hypoglycemia and the VOC detected is ethanol and optionally 1 or more additional VOCs. In certain embodiments, the physiological status is hypoglycemia and the VOC detected is methanol and optionally 1 or more additional VOCs. In certain embodiments, the physiological status is hypoglycemia and the VOC detected is propanol and optionally 1 or more additional VOCs. In certain embodiments, the physiological status is hypoglycemia and the VOC detected is methane and optionally 1 or more additional VOCs.

In certain embodiments, the physiological status is hypoglycemia and the VOC detected is propane and optionally 1 or more additional VOCs. In certain embodiments, the physiological status is hypoglycemia and the VOC detected is ethyl benzene and optionally 1 or more additional VOCs. In certain embodiments, the physiological status is hypoglycemia and the VOC detected is O-xylene and optionally 1 or more additional VOCs. In certain embodiments, the physiological status is hypoglycemia and the VOC detected is M/P-xylene and optionally 1 or more additional VOCs. In certain embodiments, the physiological status is hypoglycemia and the VOC detected is formaldehyde and optionally 1 or more additional VOCs. In certain embodiments, the physiological status is hypoglycemia and the VOC detected is acetaldehyde and optionally 1 or more additional VOCs.

Although many volatile organic compounds (VOCs) can be detected by the breath alert device 10, other respiratory aerosols can be detected as well. For instance, in addition to endogenous metabolites and exogenous compounds, droplet and aerosols including proteins, viral DNA/RNA, viral particles, non-volatile metabolites and even drugs or alcohol can be detectable. For example, $C_{15}H_{30}$ 1-pentadecene, 3-methyl-1-butanal, octane, acetic acid, alpha-pinene, and m-cymene are elevated in active ulcerative colitis. In another example, VOCs such as pentanoic acid, hexanoic acid, phenol, methyl phenol, ethyl phenol, butanal, pentanal, hexanal, heptanal, octanal, nonanal, and decanal—may be present at significantly higher concentrations in cancer groups than in the noncancer controls. Others may include VOCs such as acetaldehyde, styrene, decane, isoprene, benzene, 2,3,3-trimethylpentane, 2,3,5-trimethylhexane, 2,4-dimethylheptane, 4-methyloctane, acetaldehyde, 3-methylbutanal, n-butyl acetate, acetonitrile, acrolein, methacrolein, 2-methylpropanal, 2-butanone, 2-methoxy-2-methylpropane, 2-ethoxy-2-methylpropane, hexanal, 2-ethyl-1-hexanol, 2-methylpenthane, acetaldehyde, 2-methylpropanal, 3-methylbutanal, 2-methylbutanal, hexanal, n-butyl acetate, 2-pentanone, 2-methyl-1-pentene, 2,4-dimethyl-1-heptene, acetone, ethanol, isobutene, n-octane, tert-butyl methyl ether, tert-butyl ethyl ether, n-butyl acetate, 3-methylbutanal, 2-methylpropanal, methacrolein, 2-methyl-2-butenal, 2-ethylacrolein, pyrrole, dimethyl succinate, 2-pentanone, phenol, 2-methylpyrazine, 2-hexanone, acetophenone, benzophenone, maltol, dimethyl disulfide, methanethiol, 1-butanol, acetonitrile, cyclohexanone, tributyl phosphate, 2-methyl-1-propanal, benzyl alcohol, styrene, decanal 2-pentadecanone, nonadecane, eicosane, benzaldehyde, 2-ethyl-1-hexanol, 2,4-decadien-1-ol n-propyl benzene, 1-ethyl-2-methylbenzene, styrene, dodecane, cyclohexanol, decanal, nonanal, 1,3-Di-tert-butylbenzene, tetradecane, 2-ethyl-1-dodecanol, 2-ethylhexanol, benzaldehyde, acetophenone, 2-Ethyl-m-xylene, 1-methyl-2-pyrrolidinone, and heneicosane.

The wearable analyte breath alert device 10 comprises an outer casing 16, a forward face 12, a rear face 24, a reversible core 11, a volatile organic compound (VOC) sensor 38 and a securement means 14 adaptable to attach with the outer casing 16. The forward face 12 and the rear face 24 are secured to the outer casing 16. The forward face 12 includes an in-line insignia 13, a front port 18 and an activation button 20. The front port 18 is configured to function as gas sensing port, speaker port and lidar sensor port. The activation button 20 is configured to activate a device function. The device function includes indication of the device battery level, setting the alert levels etc. The rear face 24 is opposite to the forward face 12 and includes a detector threshold region 22, a side port 34 and an LED indicator 54. The detector threshold region 22 includes a plurality of circular holes 94 which is configured to function as gas sensor intake ports, speaker ports, Bluetooth sensors and/or cooling ports or ports for purging a previous sample. The ports may also include a means for evacuating a previous sample and for the user's breath to exit the device. The reversible core 11 includes a main processor module 72 and the reversible core 11 is positioned in between the outer casing 16, the forward face 12 and the rear face 24. The volatile organic compound (VOC) sensor 38 is adaptable to detect at least one volatile organic compound of the user. The VOC sensor 38 is positioned on the main processor module 72. The VOC sensor 38 further comprises a central sensor circuit 70 operably connected to a Bluetooth Low Energy (BLE) element 56 having a microcontroller (MCU), an alarm component 50 and a DC to DC element 42. The central sensor circuit 70 includes a gas sensor unit 86 having at least one nano gas sensor 64 and at least one heater 66, a sensor signal conditioning unit 88 having a gain element 60 and a conversion element 62, and an A/D interface 90 having an analog to digital converter (ADC) 58 and a digital to analog converter (DAC) 68. The alarm component 50 includes an audio piezo actuator 52, a vibration element 48, and a tri-color light emitting diode (LED) 54. The DC to DC element 42 includes a battery charger 40 and a battery 46. The securement means 14 is a neck securement means. The breath alert device 10 of the preferred embodiment is a necklace.

Figure 1A:
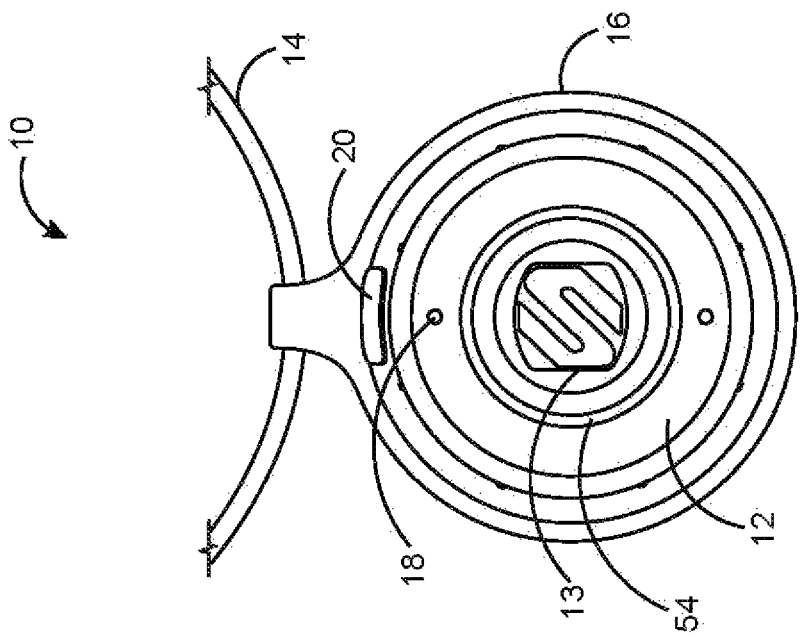
FIG. 1A illustrates a front view of a wearable analyte breath alert device for non-invasive monitoring of an analyte in a sample from a user in accordance with the preferred embodiment of the present invention.

FIGS. 1A and 1B illustrate the forward face 12 of the wearable analyte breath alert device 10 which includes the in-line insignia 13, the front port 18 and the activation button 20. The front port 18 is configured to function as gas sensing port, speaker port and lidar sensor port. The outer casing 16 of the breath alert device 10 is made of materials selected from a group consisting of: plastic, neoprene, leather complexed with plastics, waterproof materials, polyvinyls, and the like. In some embodiments, the in-line insignia 13 and the circular portion around the in-line insignia 13 can take on a variety of mechanical sensations, colors, and designs. In one embodiment, the front port 18 is utilized as an intake leading to the at least one nano gas sensor 64 and the central sensor circuit 70. In other embodiments, the front port 18 is utilized as a speaker port or a means to communicate with the user's phone 44 or an alternate device. In some embodiments, the front port 18 is utilized for many functions including but not limited to speaker port, gas sensing port, BLE transmitter, lidar sensor port, and/other sensors and ports known in the art. In some embodiments, the activation button 20 provides a means of user interface with the VOC sensor circuit 70, permitting the user to set high glucose and low glucose alert levels, set alert types, control the units of display, and the like.

As shown in FIG. 1B, the front perspective view of the wearable analyte breath alert device 10 shows the relatively thin mechanical design of the wearable analyte breath alert device 10. This design, of the present application, ensures that the user is not encumbered by a bulky, heavy gas sensing device; a problem faced by other glucose sensing devices known in the art.

As illustrated in FIG. 1A, the forward face 12 of the breath alert device 10 may include the LED indicator 54. The LED indicator 54 comprises colored lights shown as a means of electronic communication at different intensities, flashing frequencies, and colors (i.e., blue coloration, red coloration, green coloration, and the like). The electronic communication may indicate low battery, high glucose level alert, low glucose level art, battery charging indicator, pairing indicator, and the like.

Figure 1D:
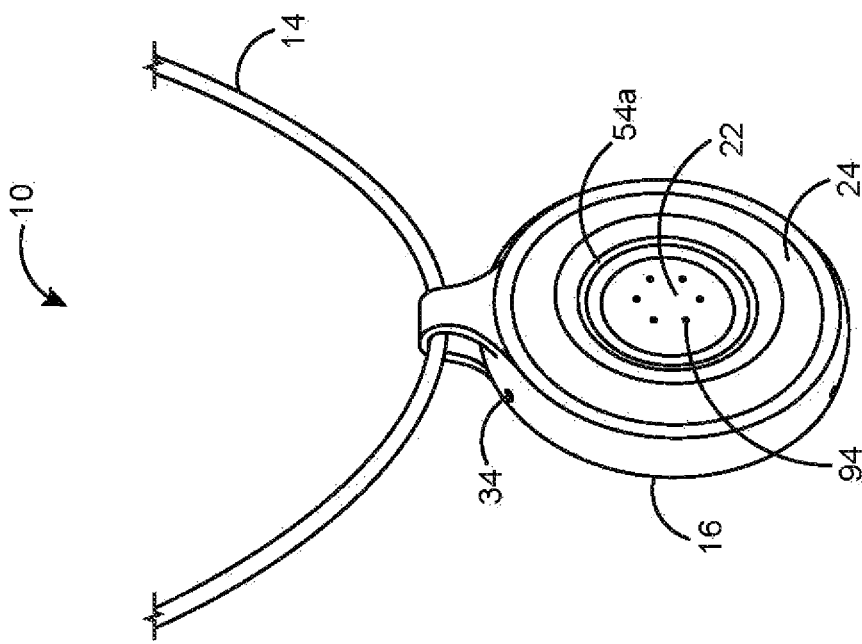
FIG. 1D illustrates a rear perspective view of the wearable analyte breath alert device with a higher intensity LED indicator in accordance with the preferred embodiment of the present invention.
Figure 1C:
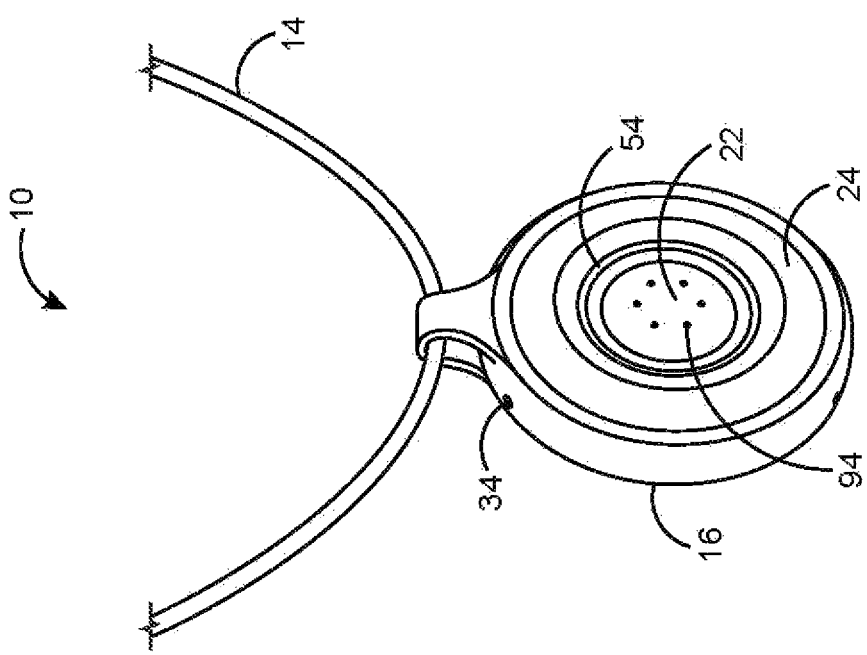
FIG. 1C illustrates a rear perspective view of the wearable analyte breath alert device in accordance with the preferred embodiment of the present invention.

FIG. 1C illustrates a rear perspective view of the wearable analyte breath alert device 10 in accordance with the preferred embodiment of the present invention. The rear face 24 includes the detector threshold region 22, the side port 34 and the LED indicator 54. The detector threshold region 22 functions as intake ports, speaker ports, Bluetooth sensors, cooling ports, and/other sensors and ports known in the art. Further, in some embodiments the side port 34 serve as speaker ports, Bluetooth sensors, cooling ports, sample or breath purging ports, temperature sensors, and/or other similar elements known in the art.

In FIG. 1D, the rear face 24 of the breath alert device 10 illustrates the LED indicator 54a having one wavelength yet at different light intensities (i.e., displaying an enhanced intensity of blue light in one state (in FIG. 1D) relative to another state as shown in FIG. 1C).

Figure 1E:
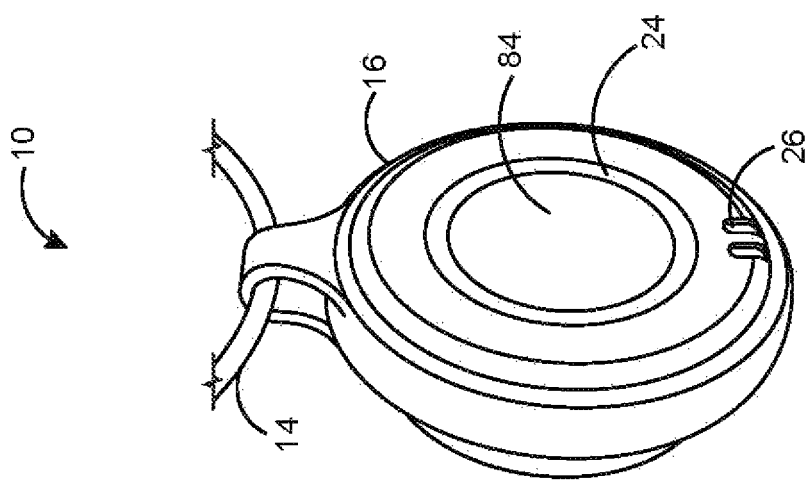
FIG. 1E illustrates a rear perspective view of the wearable analyte breath alert device with one embodiment of a detector threshold region in accordance with the preferred embodiment of the present invention.

FIG. 1E illustrates a rear perspective view of the wearable analyte breath alert device 10 with one embodiment of the detector threshold region 22 in accordance with the preferred embodiment of the present invention. The rear face 24 of the breath alert device 10 comprises the same elements as FIG. 1E except substituted with an enmeshed detector threshold region 84 more readily adapted to function as an audible speaker and/or to more readily filter aerosolized acetone molecules. As shown in FIG. 1E, in some embodiments charging pins 26 are visible on the rear exterior, facilitating docking into a desktop or nightstand-type charging port.

Notably, the breath alert device 10 is reversible in all of its iterations, which means that the rear face 24 and the forward face 12 can be fitted interchangeably into the outer casing 16. For example, FIG. 1C shows the front perspective view of the breath alert device 10 with the rear face 24 facing away from the user's chest, but the reversible core 11 can in fact be removed from the outer casing 16 and reversed in orientation such that the insignia 13 points towards the user's chest.

Figure 2B:
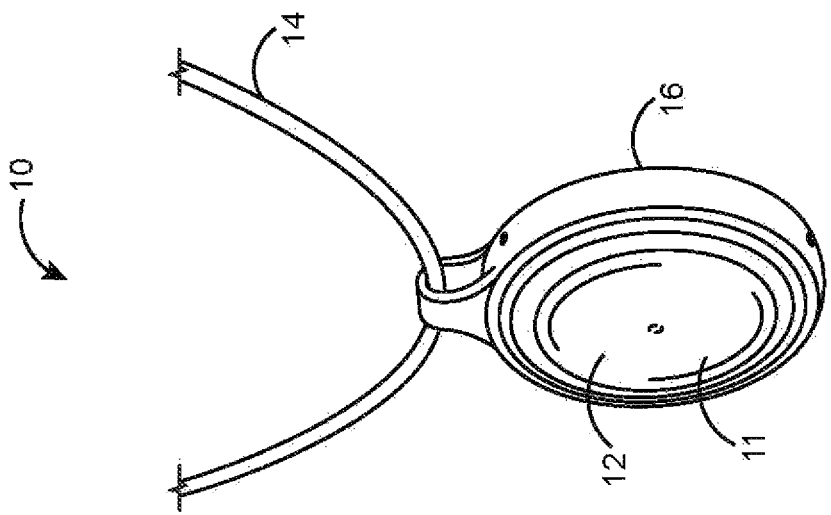
FIG. 2B illustrates a front perspective view the reversible core secured to the outer casing of the wearable analyte breath alert device in accordance with the preferred embodiment of the present invention.
Figure 2A:
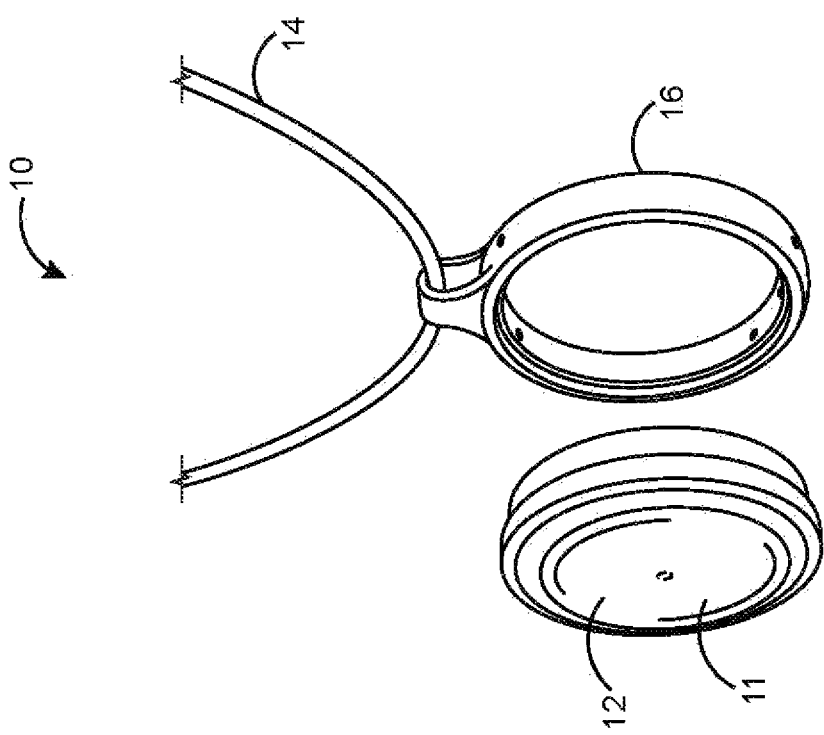
FIG. 2A illustrates a front perspective view a reversible core detached from an outer casing of the wearable analyte breath alert device in accordance with the preferred embodiment of the present invention.

FIGS. 2A-2B illustrate the front perspective views of the reversible core 11 detached from and attached to the outer casing 16 of the wearable analyte breath alert device 10 respectively. The reversible core 11 fits into the outer casing 16 by snap fit, magnetic engagement means, screw fit or the like.

Figure 3:
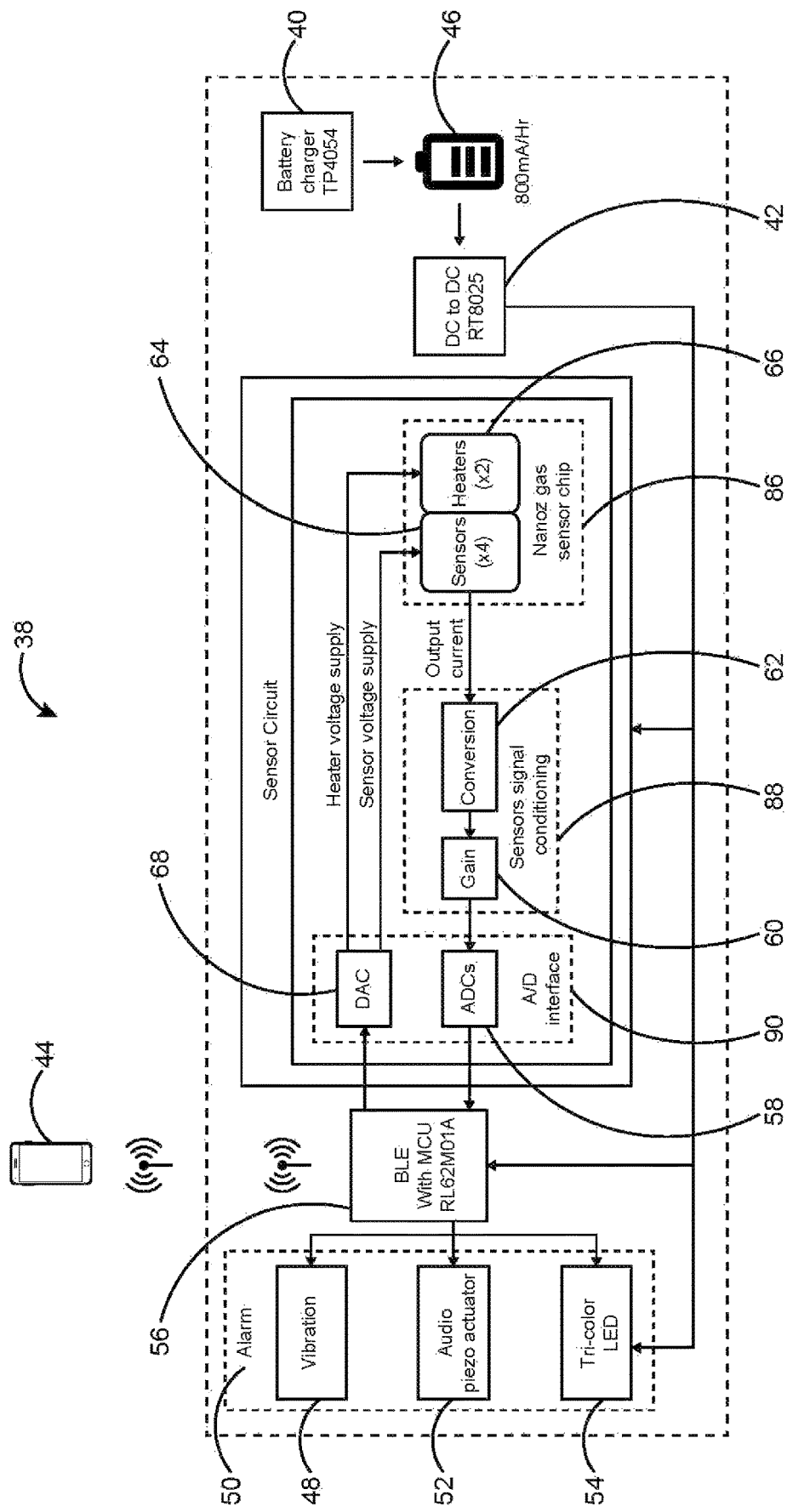
FIG. 3 illustrates a block diagram of a volatile organic compound (VOC) sensor of the wearable analyte breath alert device in accordance with the preferred embodiment of the present invention.
Figure 5:
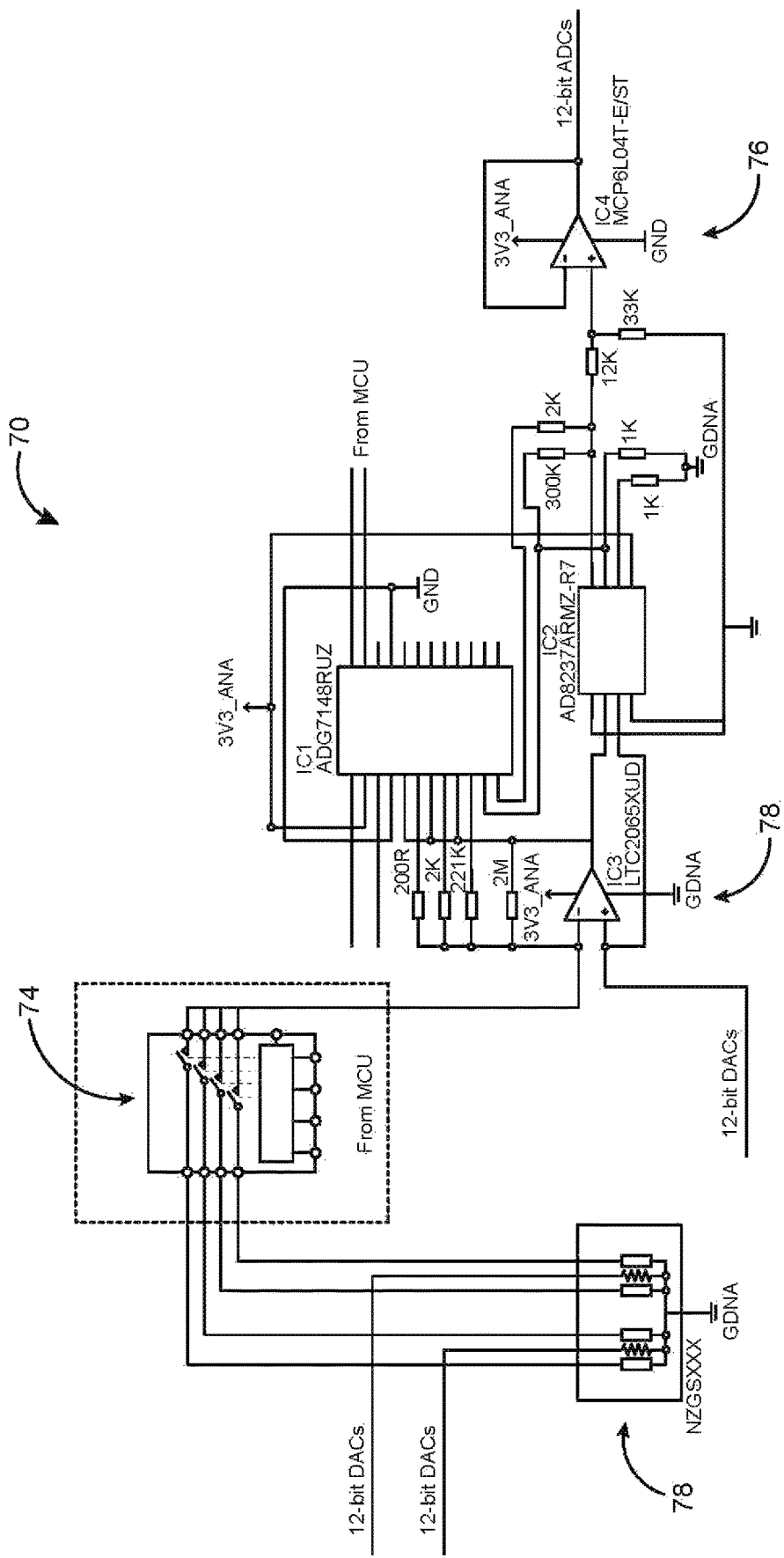
FIG. 5 illustrates a circuit diagram of a central sensor circuit of the wearable analyte breath alert device in accordance with the preferred embodiment of the present invention.
Figure 6:
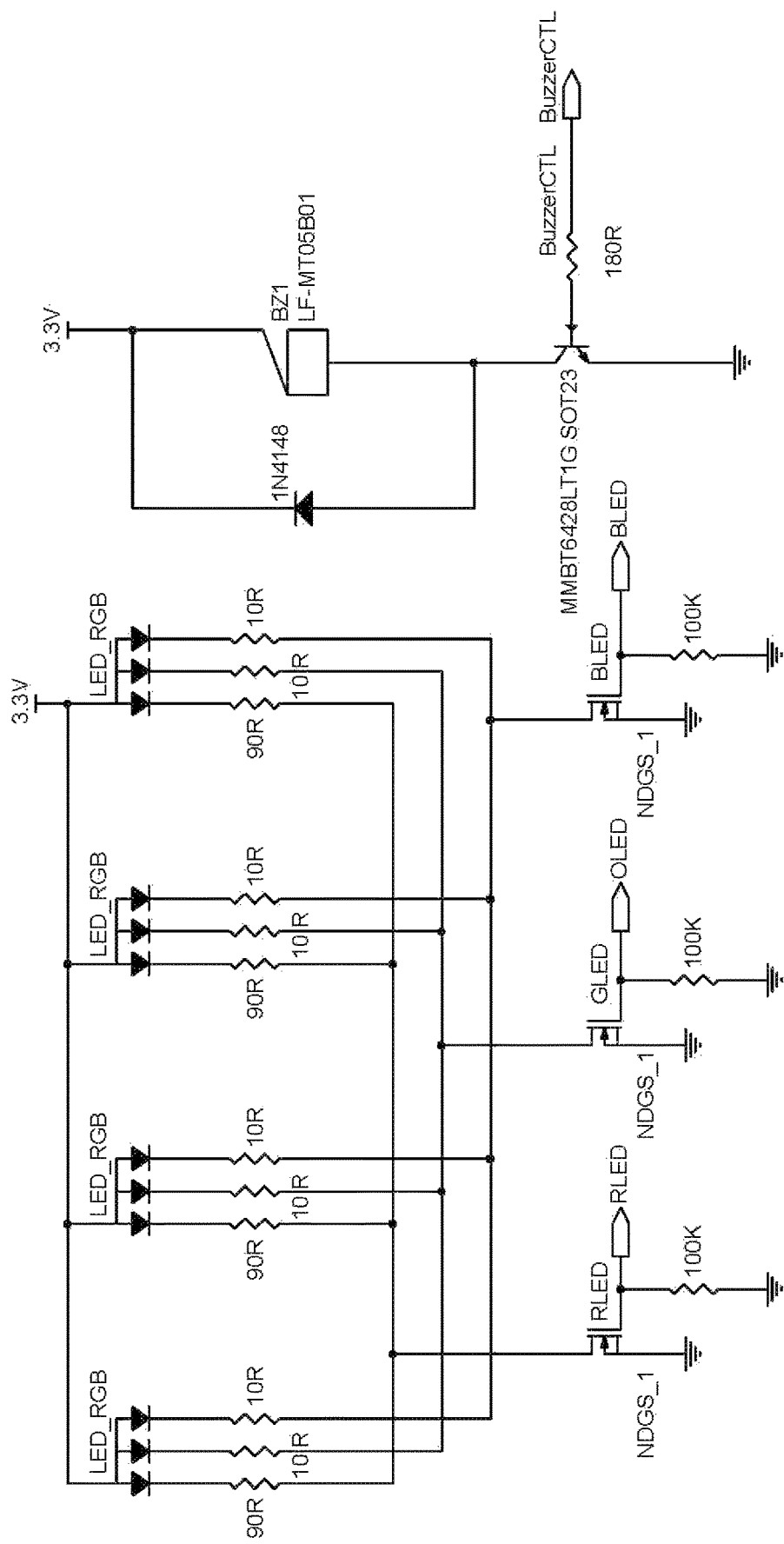
FIG. 6 illustrates a circuit diagram of an alarm component of the wearable analyte breath alert device in accordance with the preferred embodiment of the present invention.
Figure 7A:
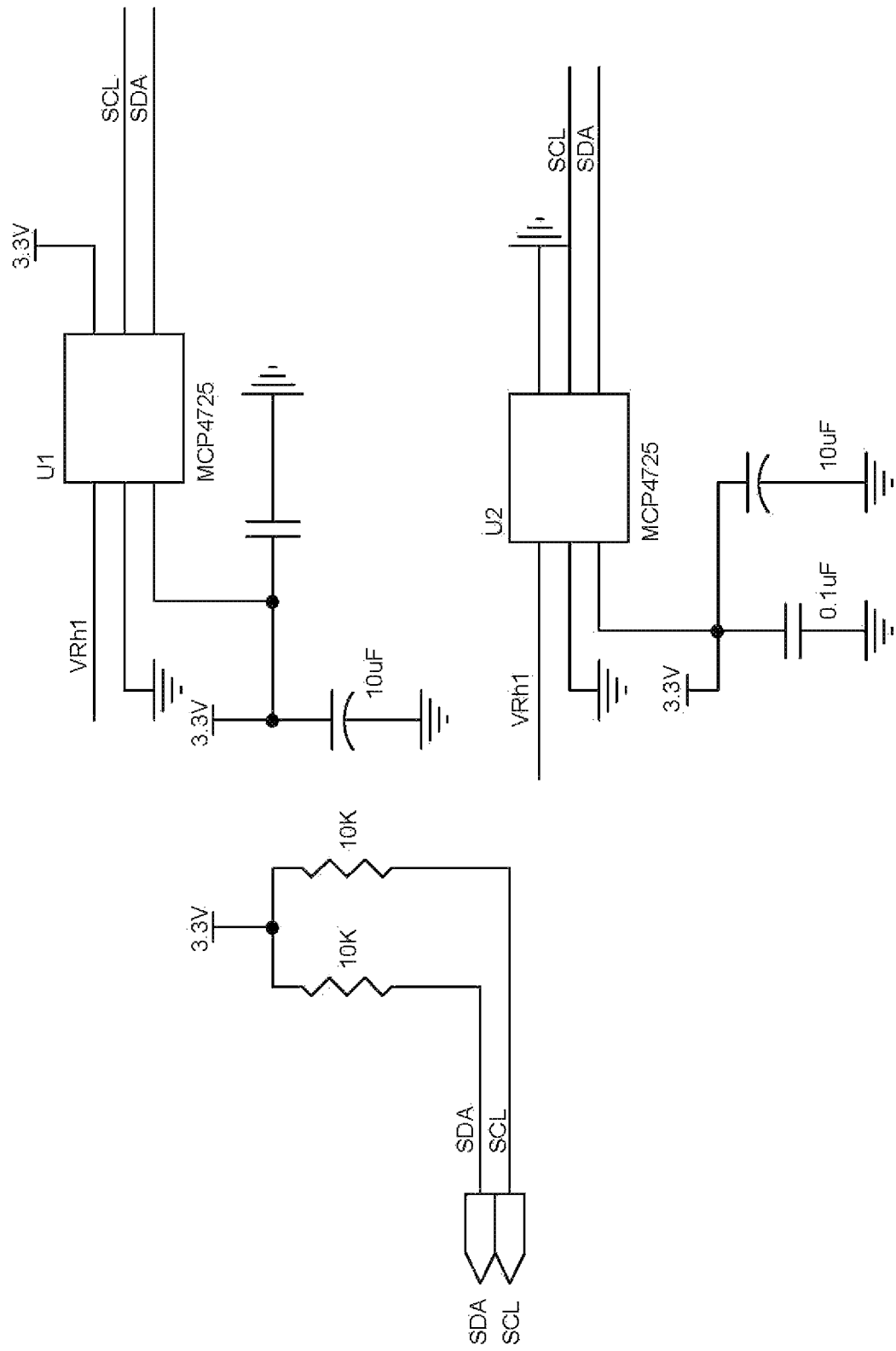
FIGS. 7A-7C illustrate a circuit diagram of a Bluetooth Low Energy (BLE) element having a microcontroller of the wearable analyte breath alert device in accordance with the preferred embodiment of the present invention.
Figure 7B:
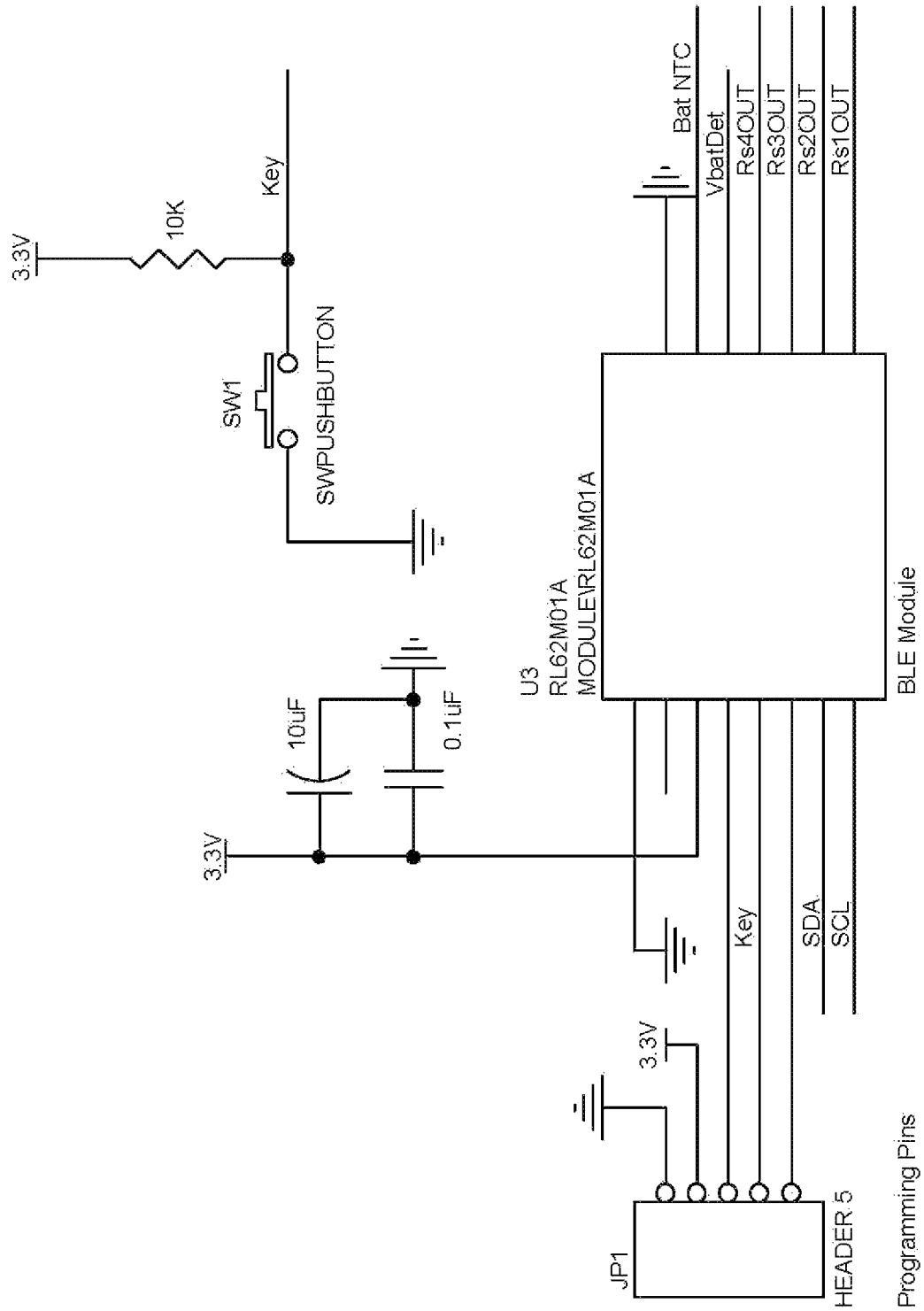
Figure 7C:
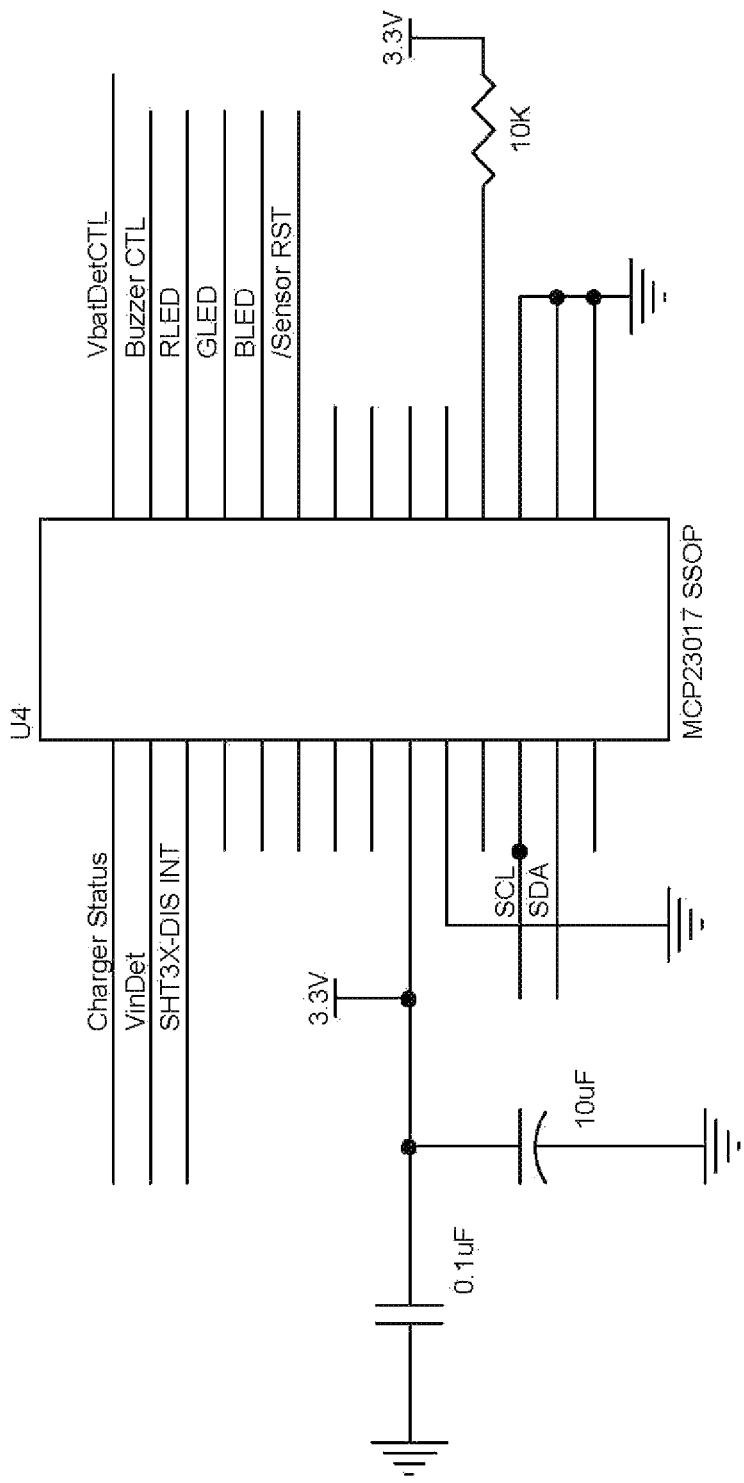
Figure 9:
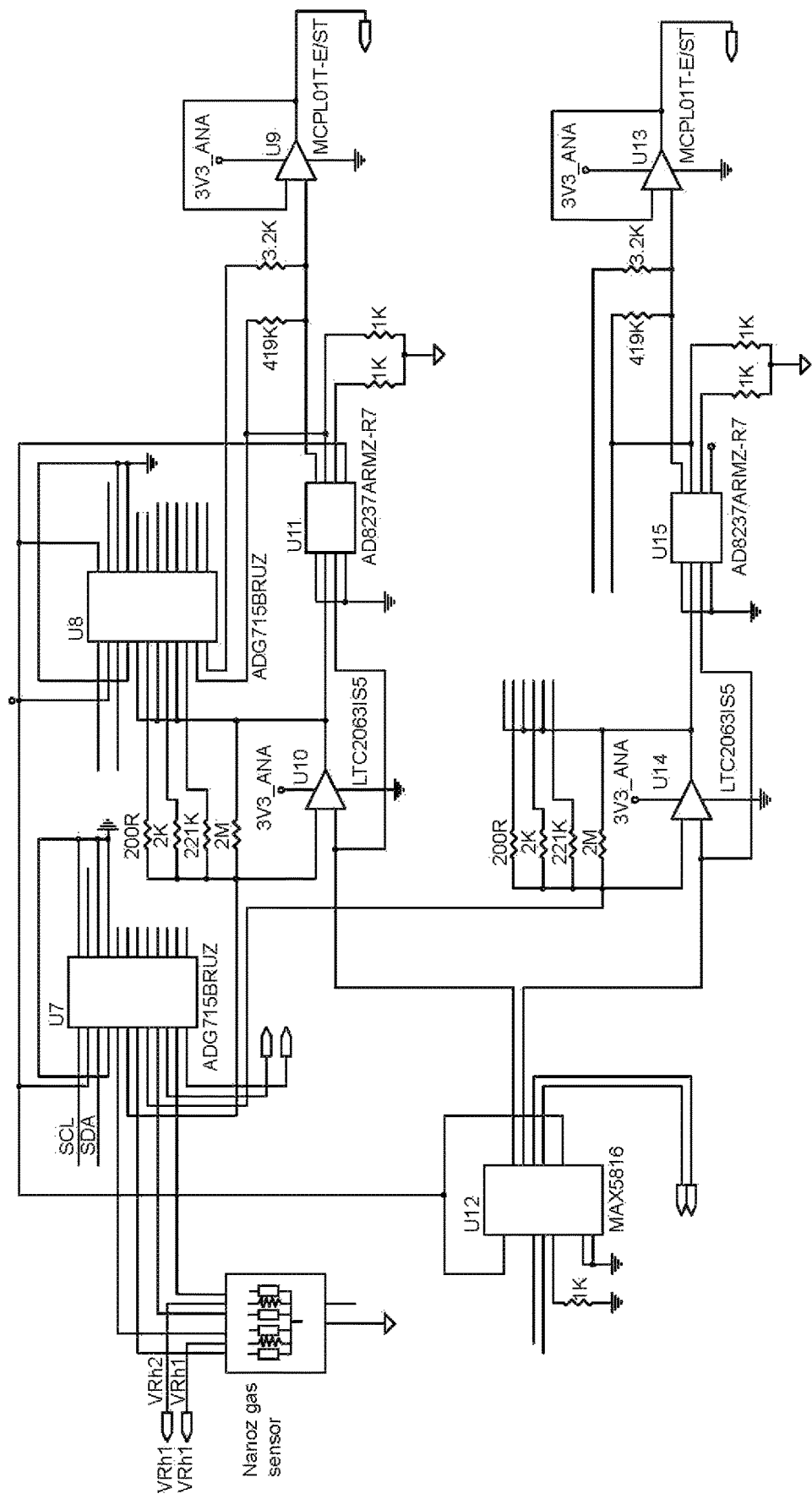
FIG. 9 illustrates a circuit diagram of a volatile organic compound (VOC) sensor of the wearable analyte breath alert device in accordance with the preferred embodiment of the present invention.

FIG. 3 illustrates a block diagram of the volatile organic compound (VOC) sensor 38 of the wearable analyte breath alert device 10 in accordance with the preferred embodiment of the present invention and FIG. 9 illustrates a circuit diagram of the volatile organic compound (VOC) sensor 38 of the wearable analyte breath alert device 10. As illustrated in FIG. 3, the VOC sensor 38 comprises the central sensor circuit 70, the alarm component 50 and a DC to DC element 42. The central sensor circuit 70 is operably connected to the BLE element 56 including microcontroller (MCU). In the preferred embodiment, the BLE element 56 utilized is RL62M01A. FIGS. 7A-7C illustrate a circuit diagram of the Bluetooth Low Energy (BLE) element 56 of the wearable analyte breath alert device 10. The central sensor circuit 70 includes the gas sensor unit 86 having the at least one nano gas sensor 64 and the at least one heater 66, the sensor signal conditioning unit 88 having the gain element 60 and the conversion element 62, and the A/D interface 90 having the analog to digital converter (ADC) 58 and the digital to analog converter (DAC) 68. FIG. 5 illustrates a circuit diagram of the central sensor circuit 70 of the wearable analyte breath alert device 10. The alarm component 50 includes the audio piezo actuator 52, the vibration element 48, and the tri-color light emitting diode (LED) 54. FIG. 6 illustrates a circuit diagram of the alarm component 50 of the wearable analyte breath alert device 10. The DC to DC element 42 includes the battery charger 40 and the battery 46 of at least 800 mA/Hr. Preferably, the DC to DC element 42 is RT8025 and the battery charger 40 is TP4054. Notably, the DAC 68 is operably connecting a heater voltage supply and a sensor voltage supply to the at least one heater 66 and the at least one nano gas sensor 64, respectively.

In some embodiments, the battery 46 includes a capacity of three to five days. In other embodiments, the estimated battery capacity is 800 mAh. In the preferred embodiment, the battery 46 has a 3000 charge-discharge life cycle. In some embodiments, the breath alert device 10 may have a battery indicator that will include a low battery feature to alert the user to recharge. In some embodiments, in case of very low battery, the breath alert device 10 may include a haptic actuator to warn of immediate impending shutdowns.

As described above, the user alerts include various alert capabilities including automated text messages, email messages, audio alerts, and haptics. In operation, upon determination of blood glucose levels, the breath alert device 10 will actuate the audio piezo actuator 52 until stopped by the user. As illustrated in FIG. 3, in one embodiment the tri-color LED 54 and the vibration element 48 permits coordinated vibration alerts and colorized alerts. FIG. 3 further depicts the central sensor circuit 70 operably connected to the BLE element 56, the audio piezo actuator 52, the DC to DC elements 42, and the battery charger 30. Further, FIG. 3 shows that, internal to the central sensor circuit 70, the DAC 68, the ADC 58, the gain element 60, the conversion element 62, the at least one nano gas sensor 64 and the heater element 66 are operably interconnected.

Figure 8A:
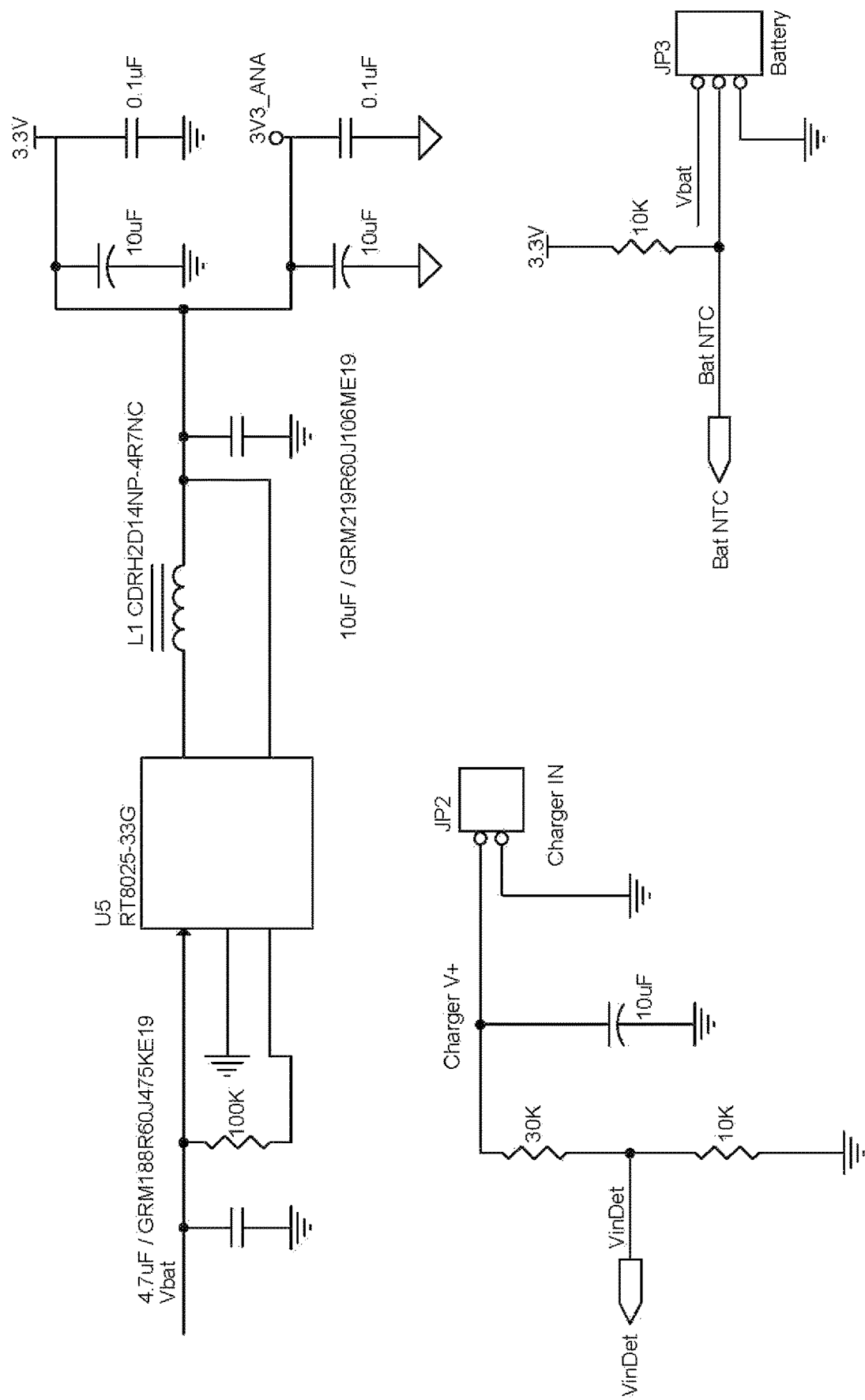
FIGS. 8A-8B illustrate a circuit diagram of a charger and power circuit of the wearable analyte breath alert device in accordance with the preferred embodiment of the present invention.
Figure 8B:
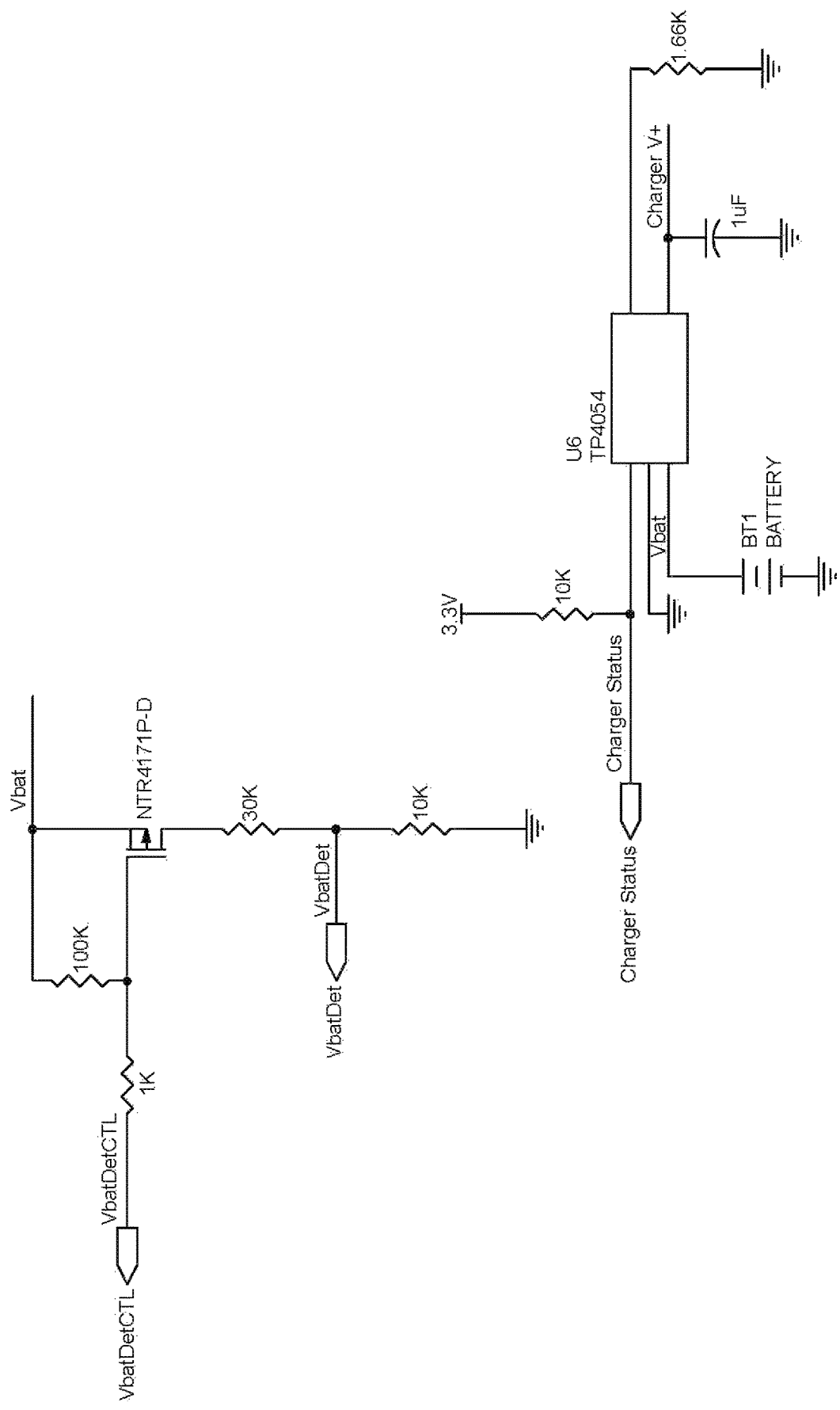

In the preferred embodiments, as shown in FIG. 3, power is supplied to the breath alert device 10 via a rechargeable 800 mAh Lithium Ion battery 46. In some embodiments, battery condition is indicated by "low", "ok", "fully charged", "time to charge", and/or similar indicators known in the art. In other embodiments, the breath alert device 10 is able to continue detection while charging on a bedside nightstand while the user sleeps. In some embodiments, the breath alert device 10 has a specified Bluetooth Low Energy connection indicator. In the preferred embodiment, the breath alert device 10 has a battery life of three to five days. In some embodiments, a charging cradle is provided in combination with the provided sensor (see FIGS. 3-4 for sensor components). Notably, charging the battery does not interfere with the device's operation, such that glucose, acetone, and other readings may be processed, stored and retransmitted during charging cycles. FIGS. 8A-8B illustrate a circuit diagram of the charger and the power circuit of the wearable analyte breath alert device 10.

Figure 4:
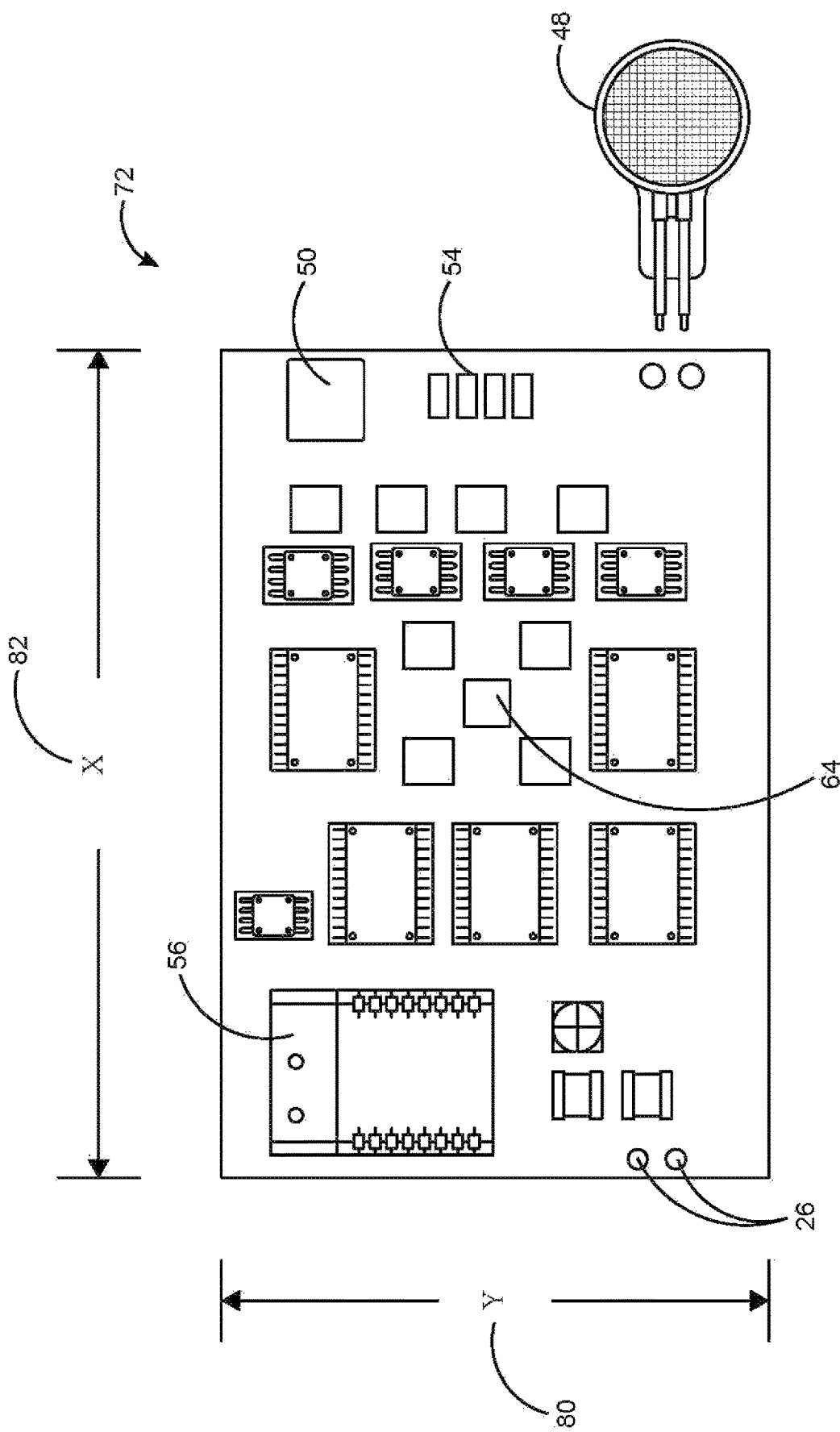
FIG. 4 illustrates a block diagram of a main processor module of the wearable analyte breath alert device in accordance with the preferred embodiment of the present invention.

FIG. 4 illustrates a block diagram of the main processor module 72 of the wearable analyte breath alert device 10 in accordance with the preferred embodiment of the present invention. The main processor module 72 includes a pair of charging pins 26, the central sensor circuit 64, a buzzer 50, a tri-color LED 54, the vibration element 48 and the BLE element 56. In some embodiments, an X axis measurement 82 of the main processor module 72 comprises at least 60 mm, 50 mm, or 40 mm in length. In some embodiments, the Y axis measurement 80 of the main processor module 72 comprises at least 40 mm, 30 mm, or 20 mm in length. In some embodiments, as depicted in FIG. 5, a SPST sensor circuit 70 is contemplated including a SPST microcontroller switches 74, an Analog to Digital Converter (ADC) 76 and a Digital to Analog Converter (DAC) 78.

As described above, FIG. 4 illustrates details of the main processor module 72. In some embodiments, the main processor module 70 includes the BLE element 56. The BLE element 56, preferably, includes RL62M01A module with 2 MBbits flash memory including a microcontroller (MCU). In other embodiments, the main processor module 72 includes auxiliary nonvolatile memory for OS backup and data recording. In some embodiments, the main processor module 72 is operably coupled to a haptic device having at least a 3G vibration rating and an operable frequency between 100 Hz and 400 Hz.

In some embodiments, the breath alert device 10 is used in a home setting. In other embodiments, the breath alert device 10 is used in a hospital setting. In some embodiments, the breath alert device 10 alerts the user via haptic, LED light array and/or voice alert and is wirelessly and operably connected to a smart device application. In the preferred embodiment, the breath alert device 10 will optionally detect a single gas (i.e., acetone) or combination of gasses emitted from the user's breath, and will indicate the presence of high or low blood sugar levels. In some embodiments, when the breath alert device 10 is out of range or otherwise not able to connect to a smart device, then it will automatically default to a "primary functions mode". In this mode, gathered information may be stored or, alternatively, may be sent to necessary third parties. In some embodiments, the user can set the high and low glucose alert levels in milligrams per deciliter (mg/dl) or in any alternative standard unit desired.

In the preferred embodiment, nano gas sensing is used for the gas sensing feature. Nano gas sensing technology includes the utilization of metal oxide semiconductors wherein a signature Volatile Organic Compound (VOC) gas is detected. In some embodiments, the user is able to set the high and low glucose alert level in milligrams per deciliter (mg/dl) and store the readings electronically in the breath alert device 10. The stored glucose level will provide an informational gauge of the user's glucose levels. Ultimately a physician is required to make clinical decisions for the user, and this technology facilitates a connection with the physician as glucose readings are readily transmissible to third parties via Bluetooth and similar technologies. In some embodiments, the breath alert device 10 is customized for monitoring patients with diabetes. Notably, the breath alert device 10 is also well-suited for (OTC) over the counter sale.

In the preferred embodiment, the nano gas sensor 64 (pre-event sensor) comprises a noninvasive ketosis analyzer. The nano gas sensor 64 is adapted to alert the user to pending changes in blood glucose levels through the analysis of reliably emitted gases from the user's breath. As shown in FIG. 3, the breath alert device 10 utilizes nano gas sensing technology wherein a signature of VOC gases can be detected by nanoliter scale-sensitive sensors. This technology utilizes metal oxide semiconductor nano sensors 64 that are extremely sensitive for detecting environmental gases. As shown in FIG. 3, the breath alert device 10 also includes an integral control board. This control board is optimized to provide both visual and audible signals.

The nano sensor 64 of the breath alert device 10 is unique in that it alerts the user in numerous ways including haptic, LED light array, programmable voice alert, and alert to a smart device via Bluetooth. These multi-modal alerts have a compounding effect; exponentially increasing the likelihood that the user will recognize the alert. Further, the user can customize the alerts to, for example, only utilize haptic alerts if an auditory signal is considered undesirable. In other embodiments, the user can choose prerecorded voice clips coupled to alerts via the speaker of the breath alert device 10, a home smart device speaker, or phone speakers.

The plurality of holes 94 of the detector threshold region 22 of the breath alert device 10 is capable of operating as both aerosol intake holes and speaker holes. In some embodiments, the alarm component 50 alerts the user when glucose levels are about to cross a preset high or low threshold stating, for instance, "you are about to experience a change in your glucose level, please take appropriate action". In some embodiments, the user can control the intensity and duration of the alarm component 50. For example, the user can choose to have a haptic signal become more intense over a period of five seconds to indicate high glucose levels, and decrease in intensity over ten seconds to indicate low glucose levels.

Figure 11:
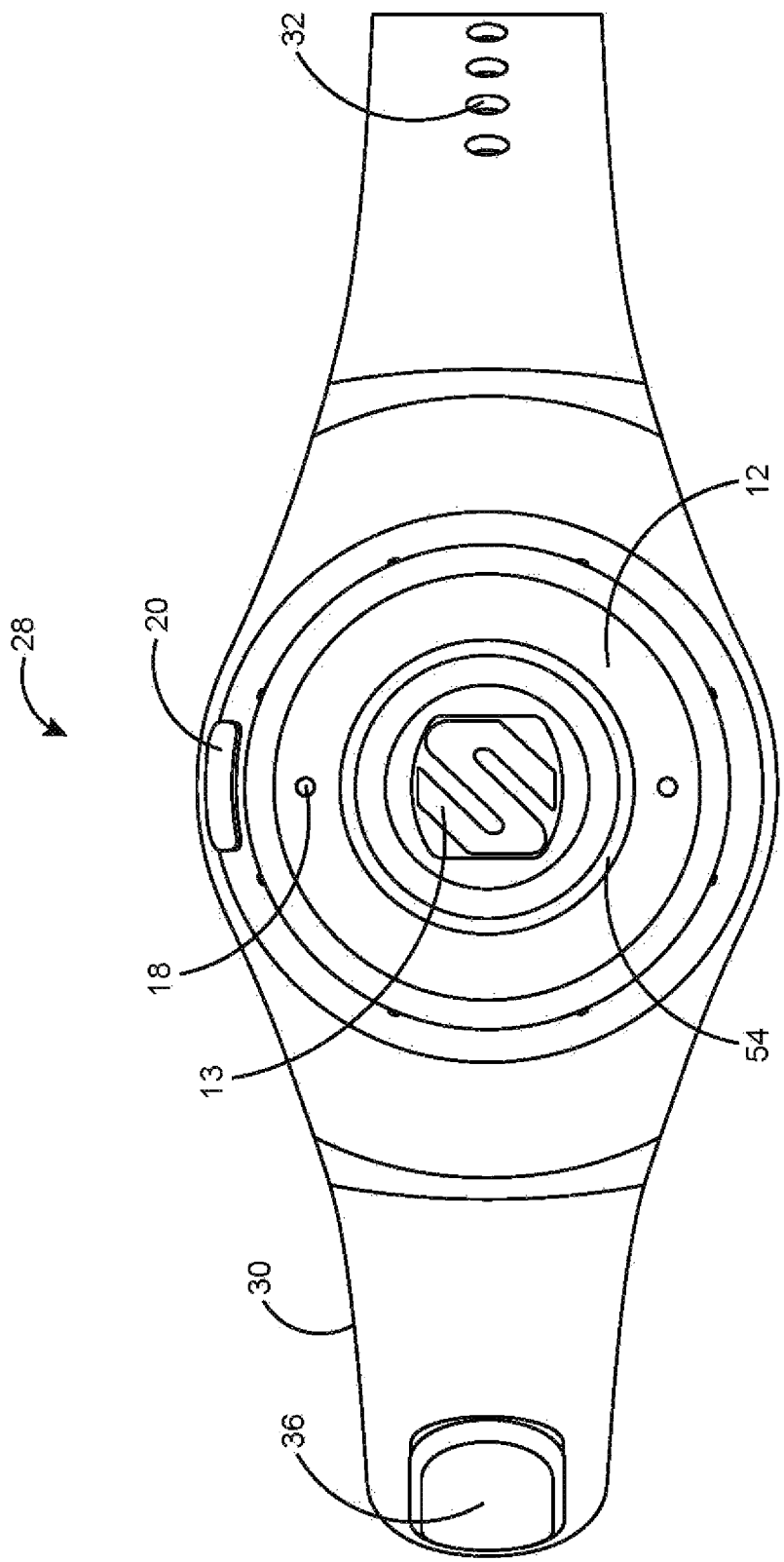
FIG. 11 illustrates a front view of a wearable analyte breath alert device in accordance with an alternate embodiment of the present invention.

FIG. 11 illustrates a front view of a wearable analyte breath alert device 28 in accordance with an alternate embodiment of the present invention. In the alternate embodiment, the wearable analyte breath alert device 28 is adaptable for use as a wristwatch. The wearable analyte breath alert device 28 includes the same reversible core 11 as that of the breath alert device 10. FIG. 11 illustrates the forward face 12 having the in-line insignia 13, the front port 18, the LED indicator 54, the side port 34 and the activation button 20 secured to a watch casing 30 having a wrist clasp 36 and a plurality of clasping holes 32.

Figure 12A:
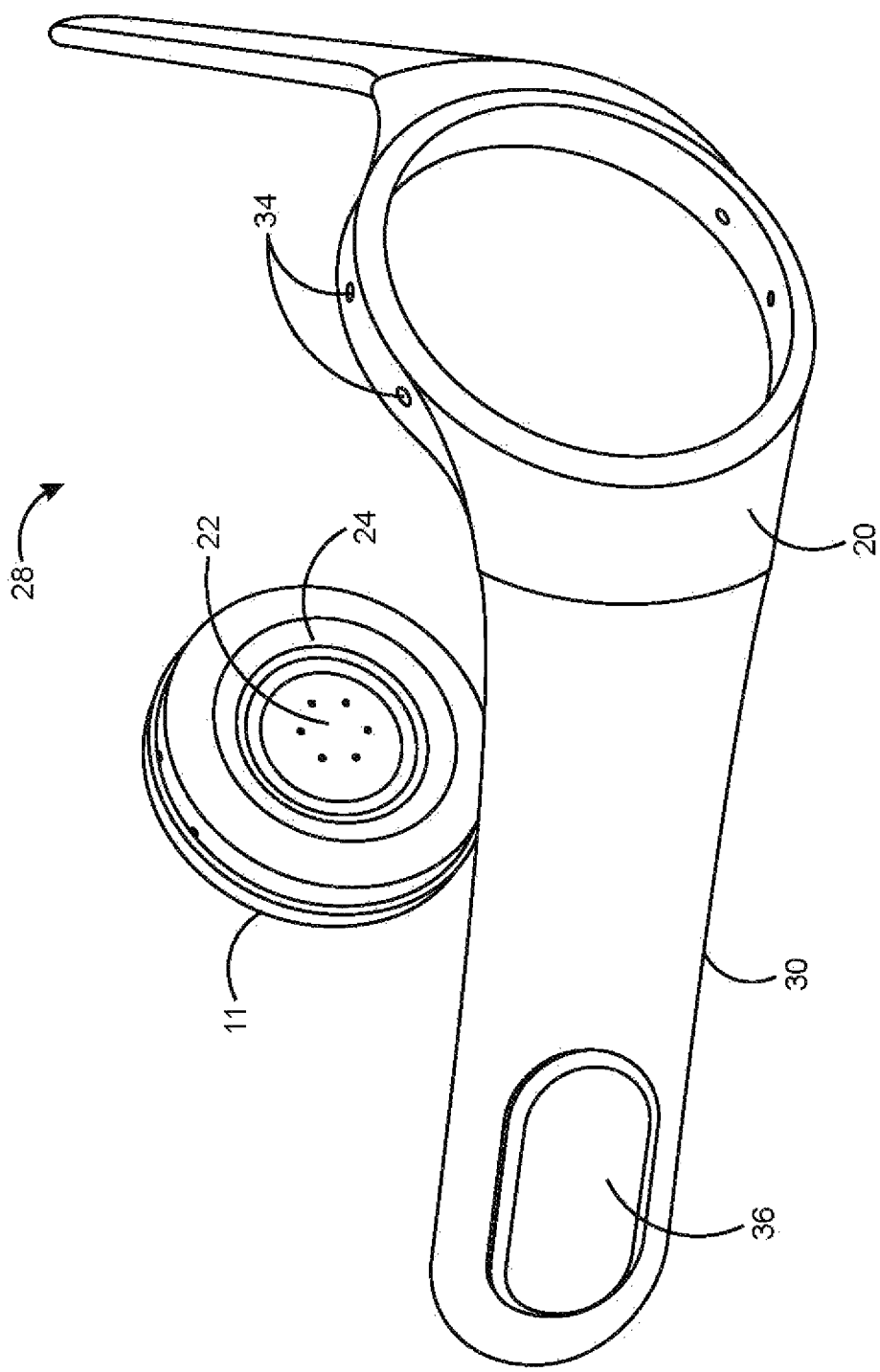
FIG. 12A illustrates a perspective view of the reversible core detached from a watch casing of the wearable analyte breath alert device in accordance with an alternate embodiment of the present invention.
Figure 12B:
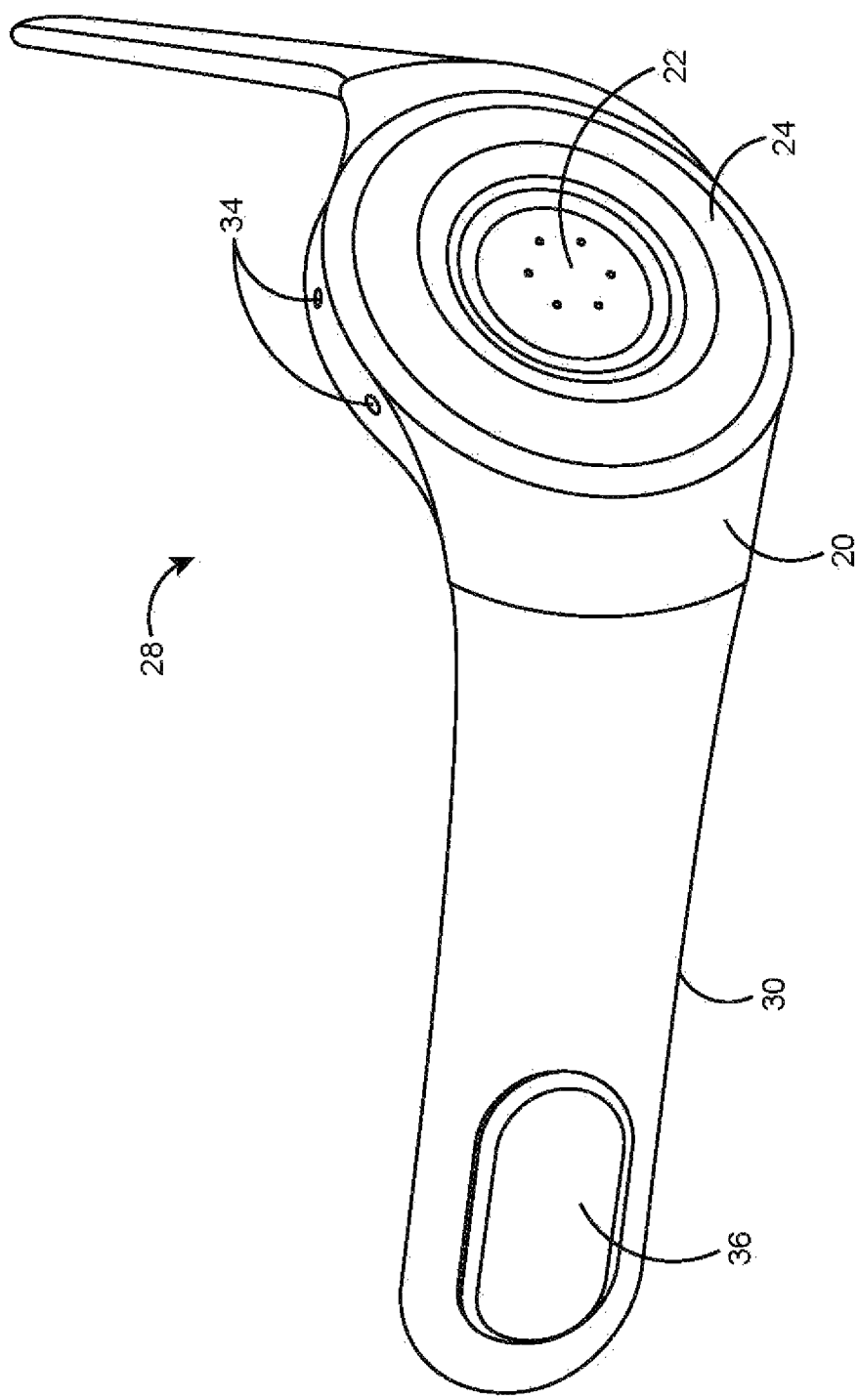
FIG. 12B illustrates a perspective view of the reversible core secured to the watch casing of the wearable analyte breath alert device in accordance with an alternate embodiment of the present invention.

FIGS. 12A and 12B illustrate perspective views of the reversible core 11 detached from and secured to the watch casing 30 of the wearable analyte breath alert device 28 in accordance with an alternate embodiment of the present invention. In FIG. 12B, the reversible core 11 is reversed, illustrating the rear face 24 having the detector threshold region 22 secured to the watch casing 30. The watch casing 30 having the wrist clasp 36 and the plurality of clasping holes 32 is made of material composed of silicone rubber, nylon or other similar adjustable material.

Figure 13C:
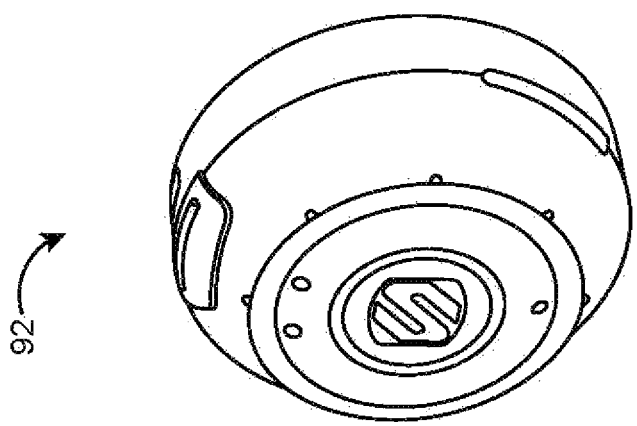
FIG. 13C illustrates a front perspective view of the wearable analyte breath alert device in accordance with another embodiment of the present invention.
Figure 13B:
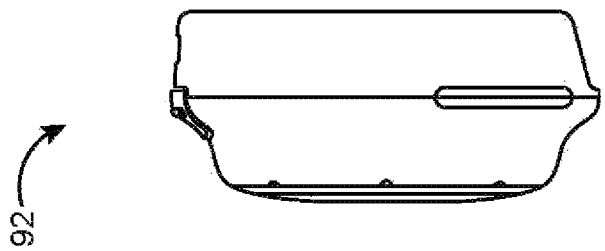
FIG. 13B illustrates a side view of the wearable analyte breath alert device in accordance with another embodiment of the present invention.
Figure 13A:
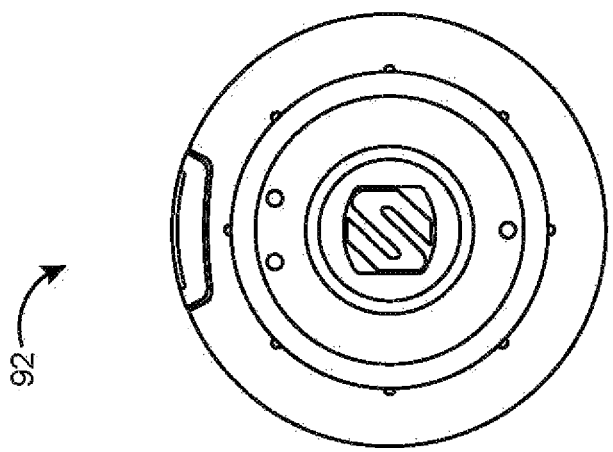
FIG. 13A illustrates a front view of the wearable analyte breath alert device in accordance with another embodiment of the present invention.

FIGS. 13A-13B illustrate a wearable analyte breath alert device 92 in accordance with another embodiment of the present invention. The breath alert device 92 of this embodiment can be clipped to the user's clothing or other personal items.

In one embodiment, the present application includes a ketone test system in which the presence of ketones is quantitated by way of measuring various aerosolized compounds (i.e., direct aerosolized ketone analysis or acetone analysis). The acetone may be derived from decarboxylation of acetoacetate, which is produced from apolysis or lipid peroxidation. The synthesis and degradation of such ketone bodies is therefore related to blood glucose levels. As is further known in the art, identification of ketones is used in the diagnosis and treatment of acidosis (a condition characterized by abnormally high acidity of body fluids) or ketosis (a condition characterized by increased production of ketone bodies such as acetone) and for monitoring patients on ketogenic diets and patients with diabetes.

In one embodiment, the outer casing 30 is in part or completely PC/ABS Plastic. As described above, in some embodiments these casing materials permit the present application to be worn as a necklace. In some embodiments, the present application operably and wirelessly syncs with a phone application adapted to pair with the breath alert device 10. In use, the pairing permits the user to calibrate measured glucose alert levels and to individually customize alert settings. In some embodiments, the alarm component 50 includes an alert timing means. The alert timing means is programmable by the user at any desired time interval. For example, the user can program alerts and the recording of glucose levels at least every 5 minutes, 15 minutes, every hour, and/or every day. In the preferred embodiment, once the breath alert device 10 is fully configured, the device 10 is operationally automated, which means that the breath alert device 10 can run, collect data, and perform all functions without the input of the user.

Further, in some embodiments the user can breathe directly into the breath alert device 10 in order to take a glucose reading. In some embodiments, directly blowing into the breath alert device 10 sets off specific mechanosensors and software systems that determine whether a change in glucose is temporally imminent. Notably, in the preferred embodiment, the nano sensor 64 of the breath alert device 10 is sensitive enough to take glucose readings from a reasonable distance such that the user is not required to blow directly into the device for all measurements. In some embodiments, when the breath alert device 10 is not able to connect via BLE element 56 (i.e., out of range, battery on smart device dead, etc.) the breath alert device 10 will continue to perform its routine functions. In this disconnected state, for example, the breath alert device 10 simply cannot transmit the collected data to the user's phone.

In some embodiments, the user identifying information is provided by the breath alert device 10 in various forms. In some embodiments, the user's name, allergy information, emergency contact information, and the like are accessible through the smartphone or smart device application software and may be automatically transmitted to emergency medical personnel in the event that certain input information is coupled in the breath alert device 10. For example, the breath alert device 10 on board trackers are adapted to measure both hypo or hyper glycemic state of the user. When this information is coupled, the user has the ability to program the breath alert device 10 to automatically call and transmit identifying information to 911, a doctor, or a loved one, and the like.

In some embodiments the device 10 will continue to take and record readings even when there is no suitable connection to any cloud service or external device. Once said connection is reestablished, the recorded readings are transmitted at that time.

In some embodiments, the audio piezo actuator 52 of the breath alert device 10 is adaptable to use with the alarm element 50. In some embodiments, the audio piezo actuator 52 has a capacity of 80 db SPL between 1 KHz and 5 KHz. In other embodiments, the LED indicator 54 comprise a high brightness LED with minimum 15 Lumen. In some embodiments, board to board connections may be made with a flat ribbon cable.

In one embodiment, the functions described in the present application may be performed under the control of a mobile application, such as a program contained on a smart phone 44 or smart watch. All of the methods and tasks described herein may be performed and fully automated by a computer system. The computer system may, in some cases, include multiple distinct computers or computing devices (including, but not limited to, physical servers, workstations, storage arrays, and cloud computing resources) that communicate and interoperate over a network to perform the described functions. Each such computing device typically includes one or more processors for execution of program instructions stored in a memory or other non-transitory computer-readable storage medium (including, but not limited to, a solid-state storage device, disk drives, thumb drive and the like). The functions disclosed herein may be embodied in program instructions. The various functions disclosed herein may be implemented in application-specific circuitry of the system. Where the computer system includes multiple computing devices, these devices may, but need not, be co-located. In certain embodiments, a result of the disclosed methods and/or tasks may be persistently stored by transforming physical storage devices, including those described herein, into a different state. In some embodiments, the computer system may be a cloud-based computing system.

In one embodiment, the functions described herein may be carried out using an algorithm designed for accomplishing such functions. The algorithm may be a part of a processor of a device of the present disclosure (in particular, a wearable device) or a part of a processor of a computer system described herein. Depending on the embodiment, the functions of any method processes or algorithms described in the present disclosure can be performed in a different sequence from that disclosed. Moreover, in certain embodiments, the functions described herein can be performed concurrently, for example, through multi-threaded processing, interrupt processing, or multiple processors or processor cores or on other parallel architectures. In certain embodiments, the functions described herein can be performed sequentially.

The illustrative logical blocks, modules, routines, and algorithm steps described in the present application can be implemented as electronic hardware (e.g., ASICs or FPGA devices), computer software that runs on general purpose computer hardware, or combinations of both. For example, various illustrative components, blocks, modules, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as limiting the present disclosure to such implementation.

The illustrative logical blocks, modules, routines, and algorithm steps described in the present application can be implemented by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination of the foregoing. A general purpose processor device can be a microprocessor, but in the alternative, the processor device can be a controller, microcontroller 56, or state machine, or combinations of the foregoing. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

In some embodiments, a variety of sensors may be used in the breath alert device 10 in addition to the nano sensor 64 described above. In one embodiment, any sensor known in the art to detect an analyte of interest may be used. In one embodiment, any sensor known in the art to detect blood glucose or a VOC of interest may be used. In another embodiment, the sensor is a semiconductor metal oxide sensor, an electrochemical sensor, a field effect transistor sensor, resistive sensors, a chemiresistive sensor, or capacitive sensors. In one embodiment, a property of each of the foregoing sensors is altered upon interaction with an analyte. In certain embodiments, the sensor may be modified to show increased sensitivity and/or selectivity by modifying the sensor to increase or decrease adsorption and/or transduction efficiency for a specific analyte, including glucose, acetone, or a VOC.

The sensor comprises a sensor material capable of detecting the analyte (for example, a VOC). The analyte, on interacting with/binding to the sensor material, causes a change in a physical property, a chemical property, and/or an electronic property of the material resulting in a signal. In one embodiment, the signal is directly correlated to the presence, amount, or concentration of the analyte in the sample. In one embodiment, the signal is a change in an electrical property, such as, but not limited to, a change in conductivity (resistance), a change in capacitance, or a change in current of the sensor material or the sensor containing the sensor material. The signal is analyzed by the microcontroller to produce a result for a given analyte.

In certain embodiments, the VOC sensor 38 comprises a plurality of sensors, with a subset of the plurality of sensors designed to detect a specific analyte (for example, a specific VOC or acetone) such that a number of distinct analytes may be detected by the sensor system.

In some embodiments, the nano sensor 64 comprises at least one sensor as described herein and a data module in communication with the sensor for storing the signal generated by the sensor. When more than one sensor is present, a data module is present for each sensor of the sensor system. The sensor and the data module may be a single element of multiple elements. The data module may transmit the signal to the controller or a separate computing device (such as a smartphone, tablet, laptop or computer) and the signal is stored and/or processed by the controller of the device or a processor of the separate computing device. Alternatively, each sensor of the sensor system transmits the signal directly to the controller of the device or to a processor of the separate computing device (such as a smartphone, tablet, laptop or computer) and the signal is stored and/or processed by the separate computing device.

In one embodiment, the nano sensor 64 described in the present application is a metal oxide sensor. Resistance of the metal oxide sensing layer is altered when target analytes are present. In operation, oxidizing gases such as nitrogen dioxide and ozone cause resistance to increase, while reducing gases like VOCs and carbon monoxide cause the resistance to go down. Regulating the heater power and/or doping the metal oxide layer can be used to adjust the selectivity of the sensors. For VOC detection, metal oxide sensors that show the highest sensitivity to reducing gasses are preferred. This typically means sensors with tin oxide, with and without dopants such as, but not limited to, tungsten, palladium, platinum, titanium, lanthanum, zinc and other dopants, heated to temperatures between 300-700 degrees C. other oxides that may be used include, but are not limited to TiC, Cr—C, MmCb, NiO, and CuO. Alternatively, metal oxide sensors that have different dopants can be used. For example, a tin oxide sensor and a tungsten-doped tin oxide sensor with or without different heater temperatures, can be used to vary selectivity to a subset of analytes.

In one embodiment, the wearable breath alert device 10, and/or method of the present application provides for the establishment of a baseline (also referred to herein as a "baseline value") for a specific user. The baseline value reflects a result determined in the absence of an analyte. The baseline value may be stored by the micro controller of the wearable breath alert device 10 and the baseline value may be subtracted from any value determined as described herein.

The wearable breath alert device 10 may also be trained to adjust a result to a particular user. In one embodiment, a result is provided by the wearable breath alert device 10. The result is stored by the breath alert device 10 and/or a separate computing device. The user then tests for the physiological status by an independent means (for example, when hypoglycemia is the physiological status, by measuring blood glucose levels by a finger prick test or other prior art test). The blood glucose level determined is provided (for example, through an application of the receiving device or an input on the wearable device). The independently determined result by the breath alert device 10 may be noted to be within an acceptable range for the physiological status or outside an acceptable range for the physiological status. The independently determined result is then matched to the result obtained with the wearable device (for example, if the result obtained with the wearable device is a concentration of six VOCs and the independently determined result is blood glucose concentration, the concentration of the six VOCs is matched to the corresponding glucose concentration). This training process may be repeated any number of times.

In certain embodiments, the training process is carried out when the breath alert device 10 is initially worn by the user. In certain embodiments, the training process is carried out after the breath alert device 10 has been worn by the user for a period of time. Neural networks, cluster analysis, and/or other artificial intelligence systems may also be used in the training process (for example, to extrapolate additional training results from the received training process). When the training process is carried out multiple times, a specific VOC or a specific combination of VOCs may be identified that correlate with the greatest accuracy and repeatability with the independently determined results. As such, through the training process, the nature of the VOCs detected for each individual may be refined over time for each user. Neural networks, cluster analysis, and/or other artificial intelligence systems may also be used in this analysis.

In addition, parameters of operation of the breath alert device 10 may be determined for the user under specific conditions or based on certain parameters associated with the tests. As such, it may be determined that certain parameters adversely impact the accuracy of a result and when such a parameter is determined to be present, the presence of the parameter may be noted in a result or the value may be discarded. In certain aspects of this embodiment, the controller determines and records a sampling parameter associated with a result. Such a sampling parameter includes, but is not limited to, i) the presence of an environmental factor; ii) a temporal factor (for example, the time at which the sampling process is initiated, terminated, and/or completed); iii) a dietary factor (for example, the time at which the user last consumed a food or beverage item or the consumption of a specific food or beverage item); and iv) a physiologic factor (for example, the time at which a specific activity undertaken by the user, the general well-being of the user); and v) a medication factor (for example, any prescription medications or nonprescription items the user may be taking). The various sampling parameters may be input by the user, such as through a receiving device, and then transmitted to the controller of the breath alert device 10 or may be obtained from a third party (for example, for environmental conditions, or may be obtained by an additional sensor on the wearable device).

Figure 10:
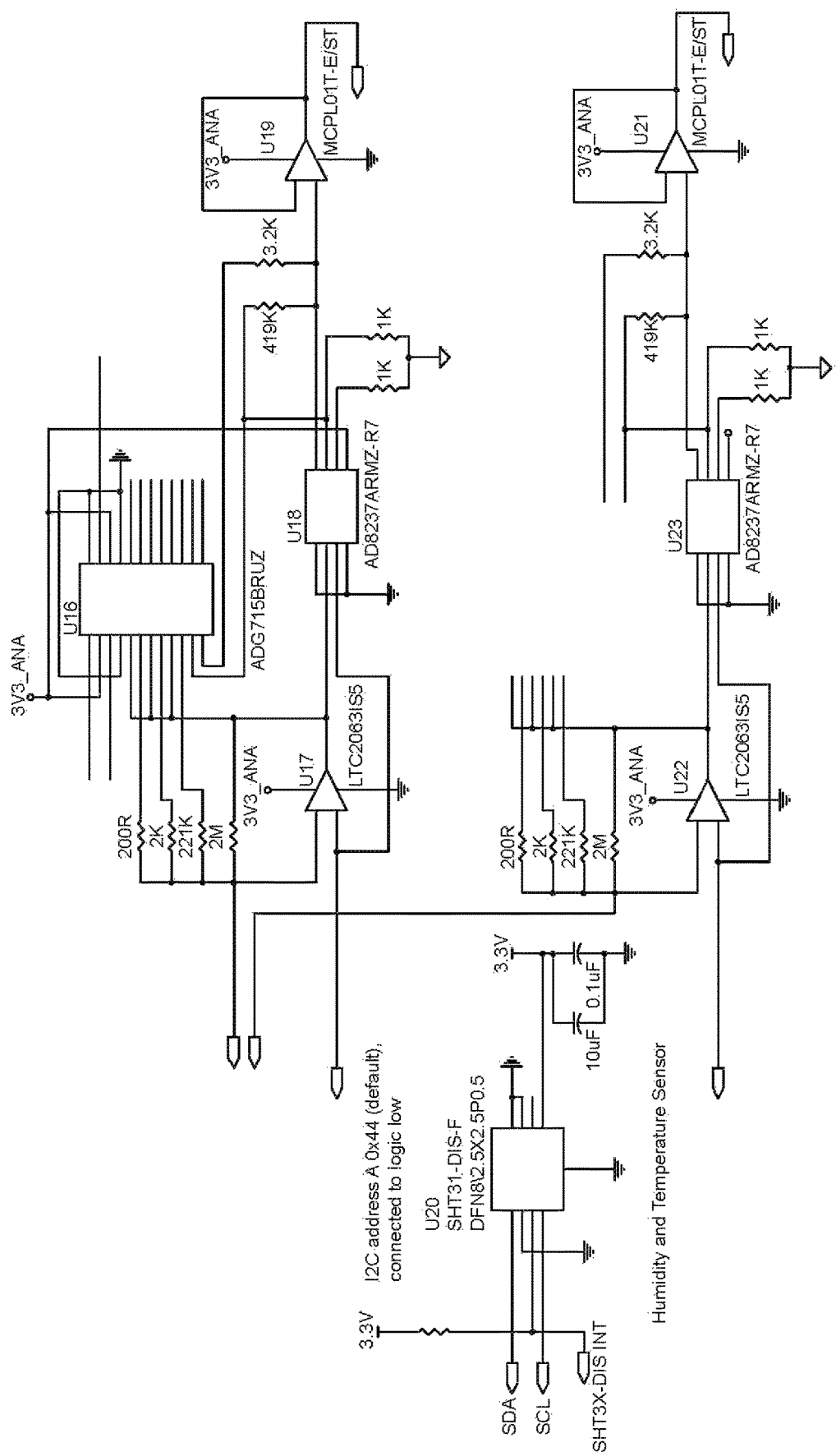
FIG. 10 illustrates a circuit diagram of a humidity and temperature sensor of the wearable analyte breath alert device in accordance with the preferred embodiment of the present invention.

The controller may tag a result with one or more of the sampling parameters. When a result obtained with the breath alert device 10 does not correlate with a result determined at the same general time by another method, the sampling parameters can be evaluated to determine if a particular sampling parameter is interfering with a result. For example, consider the following hypothetical scenario using the breath alert device 10. A result does not accurately provide for a determination of the physiological status of the user (i.e., the user is not suffering from or at risk for hypoglycemia). When the sampling parameters associated with the result are examined, it is determined that the relative humidity was over 30% and the time was 10:00 AM. In additional instances where a result did not accurately provide for a determination of the physiological status of the user, it was determined that the relative humidity was over 30% and that the time was 1:00 PM. In this hypothetical scenario, relative humidity of 30% or greater may be determined to be a sampling parameter that negatively impacts a result, while the time at which the result was determined may be determined to be a sampling parameter that does not negatively impact a result. The circuit diagram of a humidity and temperature sensor of the wearable analyte breath alert device 10 is illustrated in FIG. 10.

Figure 14:
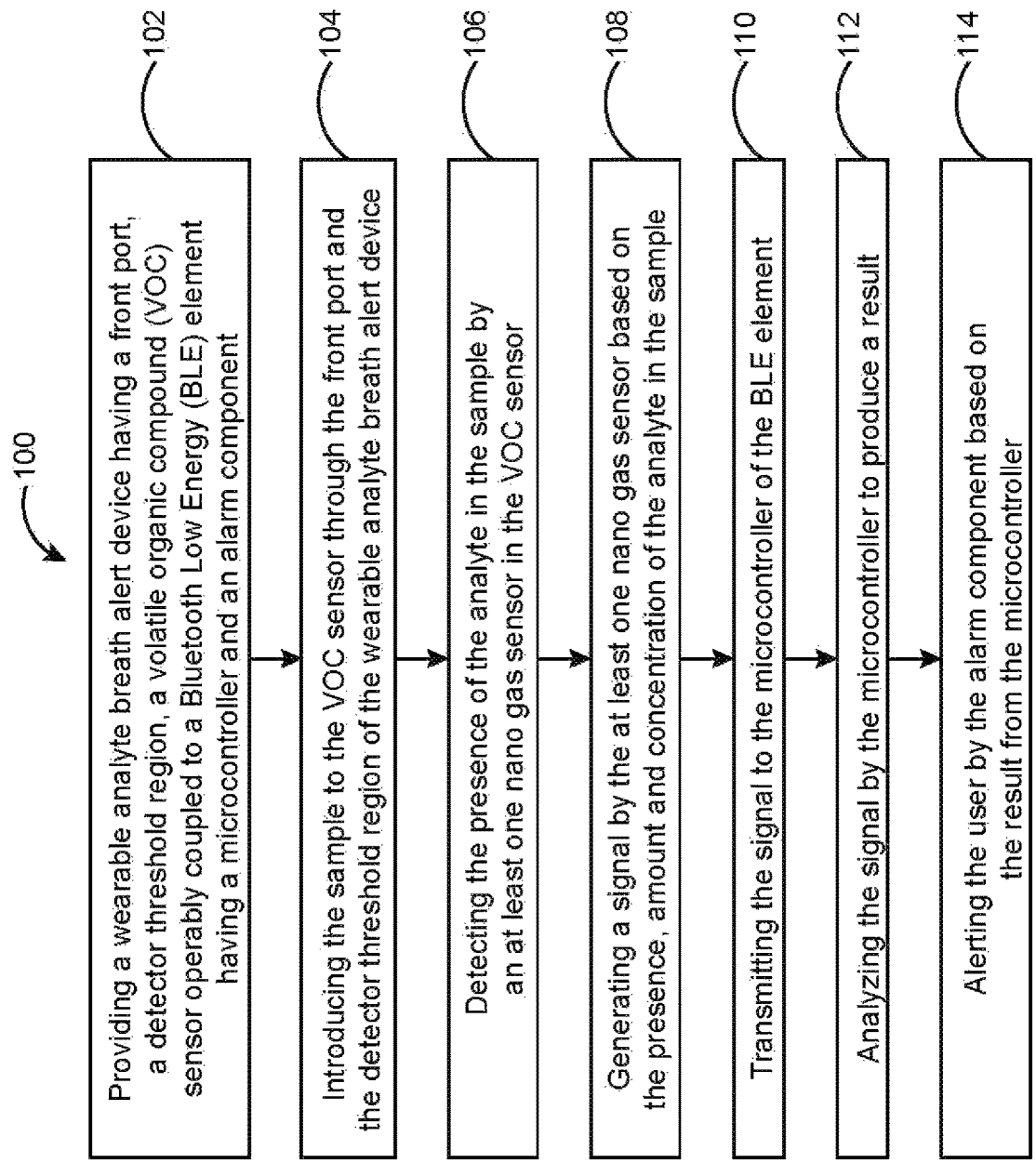
FIG. 14 illustrates a flowchart of a method for detecting acetone, ketones and other volatile organic compounds in the breath of a user utilizing the wearable analyte breath alert device in accordance with the preferred embodiment of the present invention.

FIG. 14 illustrates a flowchart of a method 100 for detecting acetone, ketones and other volatile organic compounds in the breath of the user utilizing the wearable analyte breath alert device. The present method 100 alerts the user based on the concentration of acetone, ketones and other volatile organic compounds. The method 100 comprises the steps of: providing a wearable analyte breath alert device having a front port, a detector threshold region, a volatile organic compound (VOC) sensor operably coupled to a Bluetooth Low Energy (BLE) element having a microcontroller and an alarm component for non-invasive monitoring of an analyte in a sample from a user, as indicated in block 102. Then, introducing the sample to the VOC sensor through the front port and the detector threshold region of the wearable analyte breath alert device, as indicated in block 104. Introducing the sample to the VOC sensor includes introducing the user's breath onto the front port and the detector threshold region of the wearable analyte breath alert device. The method detects the presence of the analyte in the sample by an at least one nano gas sensor in the VOC sensor, as indicated in block 106, and generates a signal by the at least one nano gas sensor based on the presence, amount and concentration of the analyte in the sample, as indicated in block 108. Then, as indicated in block 110, transmitting the signal to the microcontroller of the BLE element and analyzing the signal by the microcontroller to produce a result, as indicated in block 112. Finally, the alarm component alerts the user based on the result from the microcontroller, as indicated in block 114.

The breath alert device 10 is used by the user to monitor one or more analytes. Such monitoring allows the user to monitor his/her health status or glucose levels over time and avoid suffering from a given disease or condition. As the breath alert device 10 of the present disclosure provides information regarding the analyte without requiring the user to take steps to initiate or complete the monitoring process, the risk of non-compliance with analyte monitoring is decreased, with a resulting benefit to the health of the user.

In one embodiment, the present application provides a method for evaluating a physiological status of a user by non-invasive monitoring of the analyte in a sample from the user, the method comprising: a) providing a wearable device wherein the user wears the device; b) exposing a sensor system of the wearable device to the sample; c) detecting the analyte via the sensor system, wherein the sensor system generates a signal in the presence of the analyte; d) analyzing the signal to determine the presence, amount and/or concentration of the analyte to produce a result; e) and optionally (i) providing the result to the user; (ii) alerting the user of the result; and/or (iii) notifying the user if the result is within an acceptable range or outside of an acceptable range for the physiological status.

Another embodiment provides a method for determining if the user is suffering from, likely to suffer from, or in danger of suffering from a disease or condition by non-invasive monitoring of the analyte in a sample from the user, the method comprising: a) providing the breath alert device wherein the user wears the device; b) exposing the central sensor circuit of the wearable device to the sample; c) detecting the analyte via the sensor circuit, wherein the sensor circuit generates a signal in the presence of the analyte; d) analyzing the signal to determine the presence, amount and/or concentration of the analyte to produce a result; e) and optionally (i) providing the result to the user; (ii) alerting the user of the result; and/or (iii) notifying the user if the result is within an acceptable range or outside of an acceptable range for the disease of condition.

In one embodiment, when a physiological status is being evaluated, the physiological status is hypoglycemia. In one embodiment, when a physiological status is being evaluated, the physiological status is an infection, a respiratory infection, a urinary infection, a gastrointestinal infection, obesity, diabetes, type I diabetes, or type II diabetes. In certain aspects of the methods described herein, the non-invasive monitoring is accomplished without requiring the user to provide a direct sample to the device (for example, exhaling directly into the front port 18 of the breath alert device 10.

In certain aspects of the methods described herein, the non-invasive monitoring is accomplished without requiring the user to exhale into the front port 18 of the breath alert device 10 to initiate the monitoring process, to complete the monitoring process, determine a result of the monitoring process, and/or view such results. In certain aspects of the methods described herein, the non-invasive monitoring is accomplished without requiring an action of the user to initiate the monitoring process, to complete the monitoring process, determine a result of the monitoring process, and/or view such results.

Further, the present inventors contemplate a method to detect acetone, ketones and/or other volatile organic compounds in the breath of a user. Frist, a user is provided an apparatus including a forward face with an outer case, front port, and activation button, wherein the front port comprises an intake for a gas sensor. The user then breathes into the front port, where an electrical response is measured in the main processor module. As described above, acetone, ketones, volatile organic compounds, and other aerosolized compounds are present in the gas phase of a user's breath, enabling measurement of glucose in a user's bloodstream and noninvasive ketosis analysis. Next, an electrical response is registered due to a change in resistance of the gas sensor. A concentration measurement is then automatically recorded upon the detection of the aerosolized gas concentration (i.e., acetone, ketone and/or another volatile organic compound). This detection event is enabled by the detector threshold region, VOC sensor, SPST sensor circuit, and other components described above. Next, an alarm component alerts the user to the measurement of the detected compound at intervals controlled by the user or on demand. As noted above, the alarm component may include LED indicators, haptic alerts, vibration elements, and the like.

The wearable breath alert device 10 may be any device described herein (i.e., not limited to necklace 10 and wristwatch 28, but including clipped device 92 and other forms).

The sample may be any sample described herein. In one embodiment, the sample is an indirect sample. An indirect sample is a sample that is not introduced directly into the into the front port 18 of the breath alert device 10. In one embodiment, the sample is co-mingled with the ambient environment of the user (for example, ambient air) before being introduced into the device. In a particular embodiment, the sample is ambient air that surrounds the wearable device and the user. When the sample is ambient air, the analyte originates from or is derived from the user of the wearable device and becomes mixed with ambient air such that the target analyte is contained in the ambient air surrounding the user.

The analyte may be any analyte described herein and may be present in the sample at any concentration described herein (for example, at a concentration between 1 part per ppb and 10 ppm). In certain embodiments, the analyte is a VOC. In certain embodiments, the analyte is a VOC and the physiological status is hyperglycemia. In certain embodiments, the physiological status is hypoglycemia and the VOC detected is: (1) acetone, methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde, or any combination of the foregoing; (2) acetone, methyl nitrate, pentyl nitrate (for example, 2-pentyl nitrate), ethanol, methanol, propanol, methane, propane, ethyl benzene, isoprene or any combination of the foregoing; (3) acetone and methyl nitrate, pentyl nitrate (for example, 2-pentyl nitrate), ethanol, methanol, propanol, methane, propane, ethyl benzene, isoprene, O-xylene, M/P-xylene, formaldehyde, acetaldehyde, or any combination of the foregoing; (4) acetone and methyl nitrate, pentyl nitrate (for example, 2-pentyl nitrate), ethanol, methanol, propanol, methane, propane, ethyl benzene, isoprene, or any combination of the foregoing; (5) acetone and pentyl nitrate (for example, 2-pentyl nitrate), methanol, propane, isoprene, or any combination of the foregoing; (6) ethanol and methyl nitrate, pentyl nitrate (for example, 2-pentyl nitrate), acetone, methanol, propanol, methane, propane, ethyl benzene, isoprene, O-xylene, M/P-xylene, formaldehyde, acetaldehyde, or any combination of the foregoing; (7) ethanol and methyl nitrate, pentyl nitrate (for example, 2-pentyl nitrate), ethanol, acetone, propanol, methane, propane, ethyl benzene, isoprene, or any combination of the foregoing; (8) ethanol and methyl nitrate, ethyl benzene, or any combination of the foregoing; (9) isoprene and acetone, methyl nitrate, pentyl nitrate (for example, 2-pentyl nitrate), ethanol, methanol, propanol, methane, propane, ethyl benzene, M/P-xylene, formaldehyde, acetaldehyde, or any combination of the foregoing; 10) ethanol, methyl nitrate, and ethyl benzene; or 11) acetone, pentyl nitrate (for example, 2-pentyl nitrate), methanol, propane, and isoprene.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention to not be limited by this detailed description, but by the claims and the equivalents to the claims appended hereto.

What is claimed is:

1. A wearable analyte breath alert device for non-invasive monitoring of an analyte in a sample of aerosolized gas from a user, the device comprising:

an outer casing;
a forward face secured to the outer casing, the forward face having an in-line insignia and at least one front port, the at least one front port adapted to function as a gas sensing port or an evacuation port for evacuating a previous sample;
a rear face opposite the forward face and secured to the outer casing, the rear face having a detector threshold region, a side port and a tri color light emitting diode (LED), the detector threshold region including a plurality of circular holes configured to function as gas sensor intake ports, speaker ports, and/or sample evacuation ports;
a reversible core positioned in between the outer casing, the forward face and the rear face, the reversible core having a main processor module; and
a volatile organic compound (VOC) sensor adapted to detect at least one volatile organic compound of the user, the VOC sensor positioned on the main processor module, the VOC sensor further comprising:
a central sensor circuit operably connected to a wireless communication element having a microcontroller, the central sensor circuit including a gas sensor unit having at least one nano gas sensor and at least one heater, a conditioning circuit for conversion and gain conditioning, and an A/D interface having an analog to digital converter and a digital to analog converter;
an alarm component having an audio piezo actuator, and the tri-color light emitting diode (LED); and
a DC to DC element having a battery charger and a battery;
whereby when the user breaths out, the sample of aerosolized gas comes in contact with the VOC sensor through the at least one front port and the detector threshold region, the at least one nano gas sensor of the VOC sensor detects the analyte in the sample and generates a signal which is directly correlated to the amount of the analyte in the sample, the signal is transmitted to the microcontroller which analyzes the signal to produce a result for the analyte amount, and the alarm component alerts the user based on the result from the microcontroller.

2. The device of claim 1 wherein the analyte can be is selected from the group consisting of: glucose, acetone, and ketones.

3. The device of claim 1 further comprising an activation button that provides an interface with the VOC sensor circuit, permitting the user to set high glucose and low glucose alert levels and set alert types.

4. The device of claim 1 wherein the tri-color light emitting diode (LED) includes colored lights configured to indicate low battery, high glucose level, low glucose level, battery charging, and pairing.

5. The device of claim 1 wherein the at least one nano gas sensor is configured to detect glucose, acetone, and ketones.

6. The device of claim 1 wherein the alarm component alerts the user in at least one way selected from the group consisting of: LED light, a programmable voice alert, and an alert to a smart device via the wireless communication element.

7. The device of claim 1 wherein the wireless communication element activates the alarm component based on the signal generated by the central sensor circuit, when the at least one nano gas sensor detects the analyte in the sample.

* * * * *